(12) United States Patent
Botti

(10) Patent No.: US 8,513,188 B2
(45) Date of Patent: Aug. 20, 2013

(54) FORMULATIONS COMPRISING CYCLIC COMPOUNDS

(76) Inventor: Paolo Botti, Vessy (CH)

( * ) Notice: Subject to any disclaimer, the term of this patent is extended or adjusted under 35 U.S.C. 154(b) by 724 days.

(21) Appl. No.: 12/443,327

(22) PCT Filed: Sep. 27, 2007

(86) PCT No.: PCT/EP2007/008442
§ 371 (c)(1),
(2), (4) Date: Feb. 2, 2010

(87) PCT Pub. No.: WO2008/037484
PCT Pub. Date: Apr. 3, 2008

(65) Prior Publication Data
US 2010/0137188 A1 Jun. 3, 2010

(30) Foreign Application Priority Data

Sep. 27, 2006 (EP) ..................... 06020286

(51) Int. Cl.
| | | |
|---|---|---|
| A61K 38/00 | (2006.01) | |
| A61K 38/08 | (2006.01) | |
| A61K 38/16 | (2006.01) | |
| A61K 31/33 | (2006.01) | |
| A61K 31/335 | (2006.01) | |
| A61K 38/22 | (2006.01) | |
| A61K 38/23 | (2006.01) | |
| A61K 36/26 | (2006.01) | |
| A61P 13/12 | (2006.01) | |
| C07K 7/00 | (2006.01) | |
| C07D 267/00 | (2006.01) | |
| C07D 323/00 | (2006.01) | |

(52) U.S. Cl.
USPC .......... 514/6.8; 514/6.9; 514/13.5; 514/15.4; 514/21.3; 514/21.6; 514/183; 514/450; 530/307; 530/308; 530/324; 540/454; 549/267

(58) Field of Classification Search
None
See application file for complete search history.

(56) References Cited

U.S. PATENT DOCUMENTS

| | | | |
|---|---|---|---|
| 4,351,764 A | 9/1982 | Birr | |
| 4,474,753 A | 10/1984 | Haslam et al. | .................. 424/78 |
| 5,023,252 A | 6/1991 | Hseih | ............................ 514/183 |
| 6,444,226 B1 | 9/2002 | Steiner et al. | .................. 424/489 |
| 6,825,314 B1 | 11/2004 | Watanabe et al. | |

FOREIGN PATENT DOCUMENTS

JP 2006232909 A 9/2006

OTHER PUBLICATIONS

Darwish, I.A., et al., The Evaluation of Crown Ether Based niosomes as Cation Containing and Cation Sensitive Drug Delivery Systems, International Journal of Pharmaceutics, 1997, 159, 207-213.
Degim, I.T., et al., Effect of Ion Complexants o the Iontophoresis of Salbutamol, International Journal of Pharmaceutics, 1998, 167, 229-231.
Hamacher, K., et al., Efficient Stereospecific Synthesis of No-Carrier-Added 2-[$^{18}$F]-Fluoro-2-Deoxy-D-Glucose Using Aminopolyether Supported Nucleophilic Substitution, J. Nucl. Med., 1986, 27, 235-238.
Klein, E., et al., Carbohydrate Recognition in Water by a Tricyclic Polyamide Receptor, Angew. Chem. Int. Ed., 2005, 44, 298-302.
McGeary, R.P., et al., Cyclic Polylactones and their Cyclic Polyorthoester Valence Tautomers: Potential Ionophores, Tetrahedron, 2000, 56, 8703-8713.
Popescu, D.O., et al., The Transport Through a Liquid Membrane of Sulfadimidine and its Alkali Salts Mediated by Different Macrocyclic Carriers, Revue Roumaine de Chimie, 1998, 43(11), 1059-1064.
Touitou, E., Enhancement of Intestinal Peptide Absorption, Journal of Controlled Release, 1992, 21, 139-144.
Yang, D., et al., Cyclic Hexapeptide of D,L-α-Aminoxy Acids as a Selective Receptor for Chloride Ion, J. Am. Chem. Soc., 2002, 124, 12410-12411.

*Primary Examiner* — Noble Jarrell
(74) *Attorney, Agent, or Firm* — Pillsbury Winthrop Shaw Pittman LLP

(57) ABSTRACT

This invention relates to the use of a cyclic compound of formula (I)

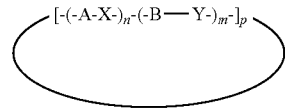

Figure 1:
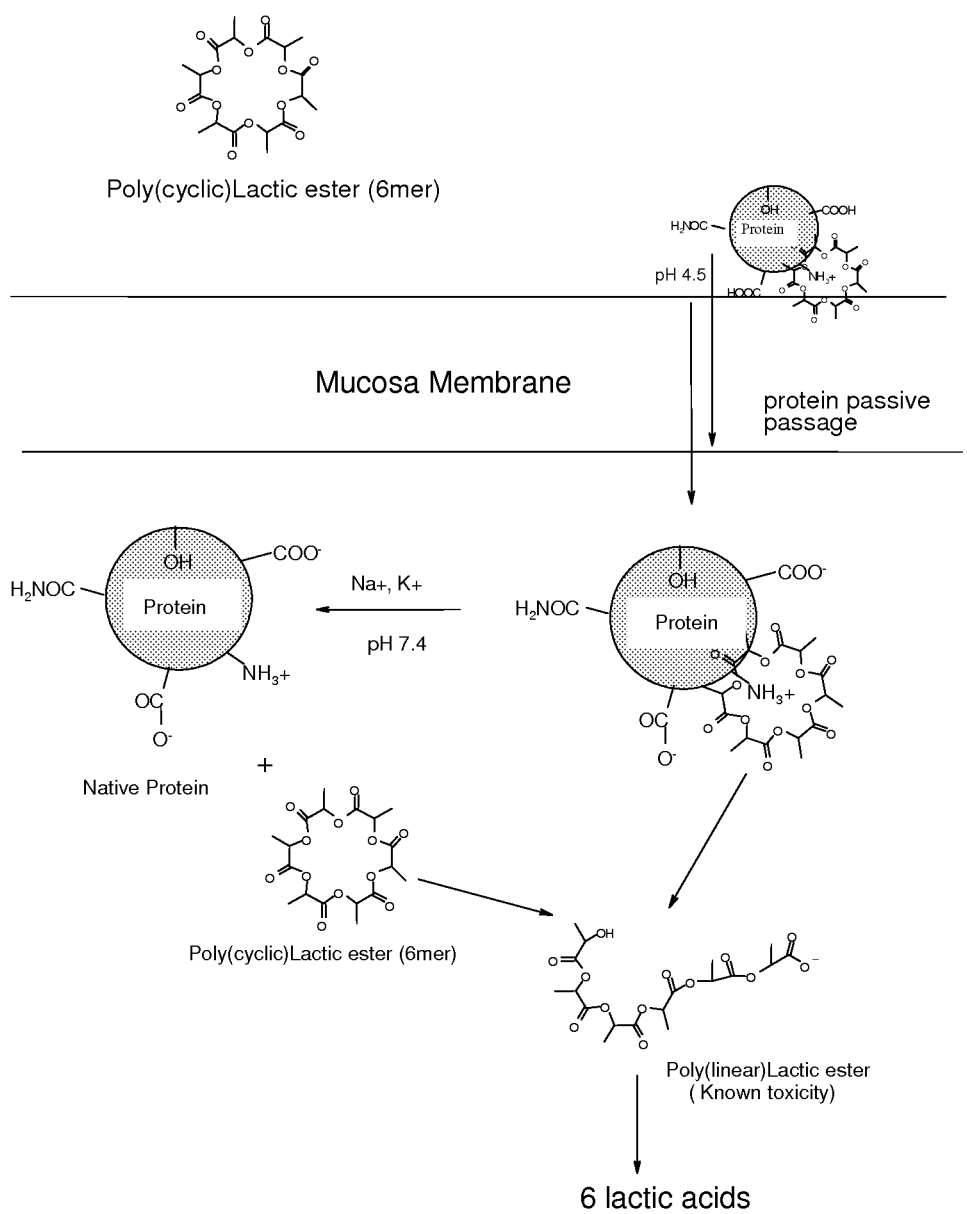

wherein A, B independently in each occurrence is alkane-i,j-diyl having k carbon atoms, i and independently j being less than or equal k and k being selected from 1 to 10, wherein said alkane-i,j-diyl (i) may comprise one or more double bonds; (ii) is optionally substituted; and/or (iii) comprises a cycle, wherein the total number of cycles being cyclic sugars in said compound is selected from 0 to 4 and is less than p·(n+m); X,Y independently in each occurrence is a biocompatible functional group comprising at least one oxygen atom or two sulphur atoms; n, m independently of each other are selected from 0 to 20; p is selected from 1 to 10; n+m is equal or greater than 1; and p·(n+m) is selected from 3 to 30; wherein said compound is capable of forming a complex with a protonated primary and/or protonated secondary amino group and/or a protonated guanidinium group for the manufacture of a pharmaceutical or diagnostic composition.

27 Claims, 10 Drawing Sheets

Nonactin

Esaglycine cyclic peptide

Poly(cyclic)Glycolic ester

Poly(cyclic)Lactic ester

Oxo Crown ethers

Sugar based crown structure 1,8,11,14,17-Pentaoxa-4,5-dithia-
cyclononadecane (S,S-Dithio crown ether)

cyclic penta aminoxyacetaldehyde cyclic penta aminoxy glycine substituted cyclic penta aminoxy glycine

FORMULATIONS COMPRISING CYCLIC COMPOUNDS

RELATED APPLICATIONS:

This application is the National Phase of International Application PCT/EP2007/008442 filed Sep. 27, 2007 which designated the U.S. and that International Application was published under PCT Article 21(2) in English, and claims priority to European Application Serial No. 06020286.8, filed Sep. 27, 2006, all of which applications are incorporated herein by reference in their entirety.

This invention relates to the use of a cyclic compound of formula (I)

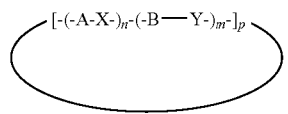

wherein A, B independently in each occurrence is alkane-i,j-diyl having k carbon atoms, i and independently j being less than or equal k and k being selected from 1 to 10, wherein said alkane-i,j-diyl (i) may comprise one or more double bonds; (ii) is optionally substituted; and/or (iii) comprises a cycle, wherein the total number of cycles being cyclic sugars in said compound is selected from 0 to 4 and is less than $p \cdot (n+m)$; X,Y independently in each occurrence is a biocompatible functional group comprising at least one oxygen atom or two sulphur atoms; n, m independently of each other are selected from 0 to 20; p is selected from 1 to 10; $n+m$ is equal or greater than 1; and $p \cdot (n+m)$ is selected from 3 to 30; wherein said compound is capable of forming a complex with a protonated primary and/or protonated secondary amino group and/or a protonated guanidinium group for the manufacture of a pharmaceutical or diagnostic composition further comprising a pharmaceutically or diagnostically active agent, said active agent comprising one or more protonated primary and/or protonated secondary amino groups and/or a protonated guanidinium groups, wherein (a) transmembrane and/or transmucosal delivery; (b) solubility in non-aqueous solvents; and/or (c) stability of said active agent are improved.

In this specification, a number of documents including patent applications and manufacturer's manuals is cited. The disclosure of these documents, while not considered relevant for the patentability of this invention, is herewith incorporated by reference in its entirety.

A increasing number of drugs is of peptidic or proteinaceous nature. This drugs in may cases have a limited shelf life and/or their administration can only be effected in an invasive manner. Intravenous administration in turn often entails significant degradation of the drug in the liver. The latter could be avoided if it were possible to deliver the drug in a manner which circumvents the degradation system of the liver. Furthermore, non-invasive administration is less cumbersome and more convenient for patients and medical staff. However, non-invasive administration, for example by the oral, buccal, sublingual, nasal, pulmonary, dermal or transdermal route is precluded because many drugs, in particular peptides and proteins, carry electrostatic charges. The presence of electrostatic charges renders cell membranes an insurmountable barrier for these drugs. Covalent modification to remove the charges may have deleterious effects, including misfolding of the polypeptide structure. An other disadvantage of covalent modification is that a compound is obtained by said modification which is distinct from the drug for which approval has been obtained.

Cyclic polyesters (polylactones) are known in the literature as cation ionophores. For example, nonactine and tetranactine are macrotetrolide antibiotics that coordinate metal ions. Other types of cyclic polyesters (polyglycolic or lactic esters) have been studied by ab initio molecular orbital calculation and have been found, depending on the number of units (size of the ring) to accommodate certain cations with some selectivity (McGeary and Bruget (2000), Lifson et al. (1983), Lifson et al. (1984)).

Synthetic polymers and copolymers of certain alpha-hydroxy acids including glycolic acid and lactic acid have been described as biodegradable plastic material for use in surgery and implants. Specific examples enjoying widespread use include the linear polymers poly(lactic), poly(glycolic) and poly(lactic-co-glycolic) acid (PLGA). In particular the latter (PLGA) is a Food and Drug Administration (FDA) approved copolymer which is used in a host of therapeutic devices, owing to its biodegradability and biocompatibility.

Cyclic polymers or oligomers of lactic acid and their synthesis have been described in EP-A1 1219616.

Cyclic polyethers are known in the literature to complex cations. For example, 18-crown-6 is a cyclic polyether known to complex many cations including $Na^+$, $K^+$ and $NH_4^+$.

Synthetic polymers and copolymers of polyethylene glycol (PEG) have been used to enhance biopharmaceutical properties of therapeutic peptides and proteins as well as vehicle for active ingredients and formulation agent.

Popescu et al. (Revue Roumaine de Chimie 43, 1059-1064 (1998)) report that complexation of inorganic salts (Na+, K+) of the sulphonamide sulfadimidine with valinomycin or certain crown ethers would result in various degrees of transport of sulfadimidine through a chloroform barrier. Popescu et al. fail to establish enhanced delivery of sulfadimidine across a biological membrane, though. Also, they use a highly artificial, namely acidic (pH=1 or 6) receiving phase which is the aqueous phase behind the chloroform barrier.

In view of the above, there is an unmet need for modifying drugs, in particular peptidic or proteinaceous drugs, to enhance their formulation and, related thereto, their administration properties. The term "administration properties" is understood to include the available routes of administration for a given active agent in a given formulation.

Given the limitations of the presently available means, the technical problem underlying the present invention was therefore the provision of means and methods for modifying the formulation properties of pharmaceutically or diagnostically active agents.

Accordingly, this invention relates to the use of a cyclic compound of formula (I)

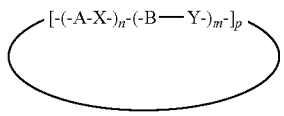

wherein A, B independently in each occurrence is alkane-i,j-diyl having k carbon atoms, i and independently j being less than or equal k and k being selected from 1 to 10, wherein said alkane-i,j-diyl (i) may comprise one or more double bonds; (ii) is optionally substituted; and/or (iii) comprises a cycle, wherein the total number of cycles being cyclic sugars in said compound is selected from 0 to 4 and is less than p·(n+m); X,Y independently in each occurrence is a biocompatible functional group comprising at least one oxygen atom or two sulphur atoms; n, m independently of each other are selected from 0 to 20; p is selected from 1 to 10; n+m is equal or greater than 1; and p·(n+m) is selected from 3 to 30; wherein said compound is capable of forming a complex with a protonated primary and/or protonated secondary amino group and/or a protonated guanidinium group for the manufacture of a pharmaceutical or diagnostic composition further comprising a pharmaceutically or diagnostically active agent, said active agent comprising one or more protonated primary and/or protonated secondary amino groups and/or a protonated guanidinium groups, wherein (a) transmembrane and/or transmucosal delivery; (b) solubility in non-aqueous solvents; and/or (c) stability of said active agent are improved.

The curved line in formula (I) stands for one single bond connecting covalently the first occurrence of A with the last occurrence of Y. The terms "first occurrence" and "last occurrence", respectively, relate to the non-cyclic counterpart of a compound of formula (I), said non-cyclic counterpart having the formula $[-(-A-X-)_n-(-B-Y-)_m-]_p$.

The term "alkane-i,j-diyl" relates to an alkane with two free valences at carbon atoms I and j. Preferred alkane-i,j-diyls are disclosed below in terms of the corresponding monomers.

It is understood that the compounds according to the invention may be characterized in either one of the following ways. First, they may be characterized in terms of building blocks A and B, wherein said building blocks are linked by functional groups X and Y. Secondly, and to the extent said functional group X, Y is further defined as being, for example, an ester group (—C(═O)—O—) or amide group (—C(═O)—NH—), compounds according to the invention may be characterized in term of the monomers giving rise to said compounds. To explain further, monomers include—in case of polyesters—hydroxy acids and—in case of polyamides—amino acids. The difference between a characterization in terms of building blocks A, B and monomers such as hydroxy acids and amino acids is as follows. The monomers include those functional groups, such as —COON, —OH in case of an amino acid monomer and —COOH, —NH2 in case of an amino acid monomer, which, upon formation of a compound of the invention from said monomers, give rise to functional groups X, Y such as ester or amide. The building blocks A and B on the other side do not include the functional groups X, Y. As a consequence, a cyclic polyester comprising monomers of lactic acid may either be characterized in terms of the monomer lactic acid or in terms of the building block A and/or B which is ethane-1,1-diyl. Similarly, the monomer glycolic acid has its counterpart in a building block A and/or which is methylene (—CH$_2$—). Accordingly exemplary/preferred values of k are 2 and 1.

The formation of a compound of the invention from said monomers may be referred to as polymerization. The term "polymerization" as used herein includes polycondensation, i.e., the formation of polymer wherein, in addition to the polymer, a low molecular weight compound such as water is formed. Furthermore, there is no lower limit on the number of monomers in a polymer according to the invention. As such, the terms "polymer" or "poly" include "oligomers" and "oligo", respectively.

Preferred alkane-i,j,-diyls include 1,k-diyls as well as alkane-i,j-diyls wherein i equals j. An example of an alkane-i,i-diyl is ethane-1,1-diyl is described above.

Figure 2:
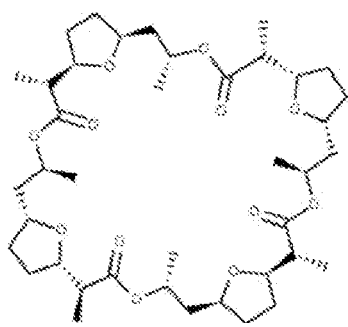
Figure 2:
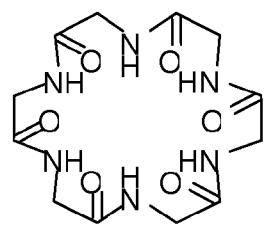
Figure 2:
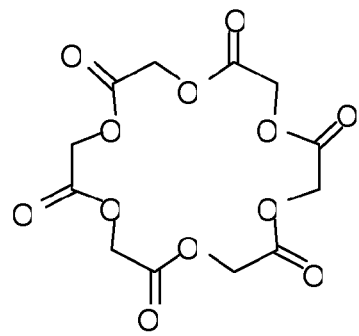
Figure 2:
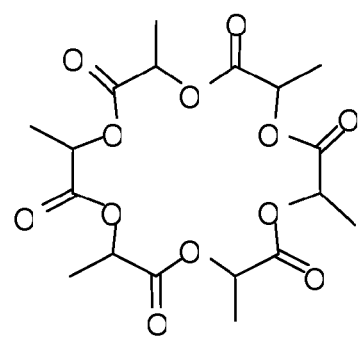
Figure 2:
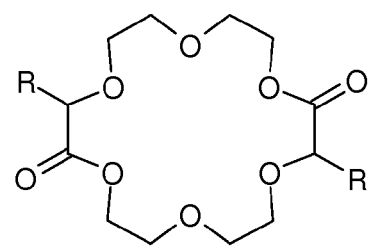
Figure 2:
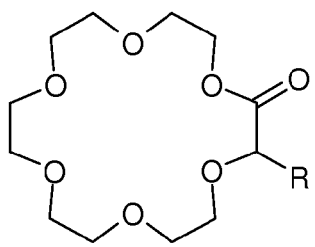
Figure 2:
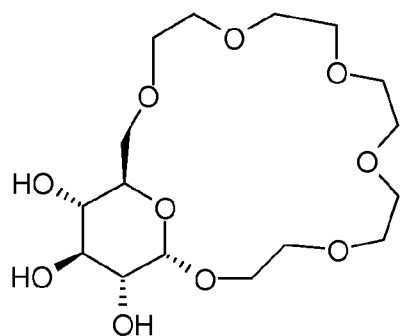
Figure 2:
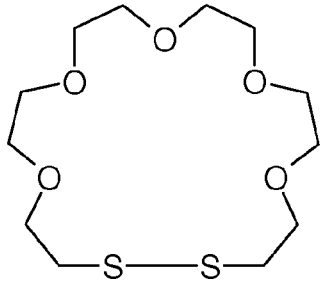
Figure 2:
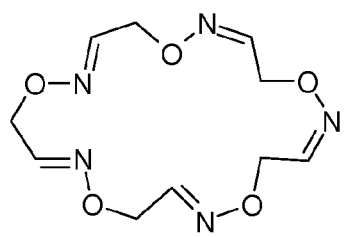
Figure 2:
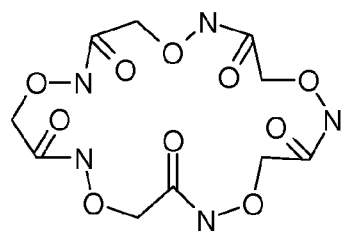
Figure 2:
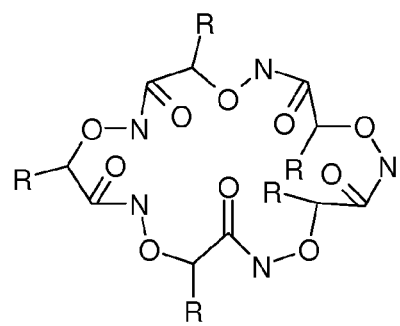

The term "substituted" is understood to include any substituents. Preferably, "substituted" refers to a mono-substitution. Preferred carbon atoms to be substituted in the alkane-i,j-diyl are carbon atoms i and/or j. It is understood that substituents, if present, introduce further carbon atoms in addition to the k carbon atoms of the alkane-i,j,-diyl into the building block A or B. In FIG. 2 enclosed herewith, substituents are designated "R".

Preferred substituents include linear or branched alkyl, preferably with between 1 and 10 carbon atoms, the linear or branched alkyl substituents optionally being substituted with one or more of —OH, —COOH and halogen. Further preferred substituents include substituted or unsubstituted aryl or heteroaryl. Preferred aryl substituents are phenyl, methylphenyl such as 4-methyl-phenyl and hydroxy-phenyl such as 4-hydroxy-phenyl. Further preferred substituents of the alkane-i,j-diyl are one or more of —OH, —COOH and halogen.

The term "cycle" refers to building blocks comprising a cyclic structure such as the building blocks of nonactin (see below). Other examples of a cycle within a monomer is the cyclic form of a sugar or of a sugar derivative. Cyclic sugars of the invention include pyranoses and furanoses such as glucopyranose. If present, the number of monomers being or comprising cyclic sugars is less than the total number of monomers of the compound of the invention. More preferred, the number of monomers consisting of or comprising cyclic sugars, if present, is 1, 2 or 3. Also, it is preferred that not more than two monomers consisting of or comprising cyclic sugars are directly linked to each other, wherein the link, i.e., the functional group X or Y, respectively, is —O—, said —O— being a glycosidic bond. The term "sugar derivative" includes sugars wherein one, more or all hydroxy groups are acetylated and/or alkylated.

It is understood that the alkane-i,j-diyl may be cyclic. Alternatively or in addition, a substituent of the alkane-i,j-diyl may be cyclic. Also envisaged are cycles comprising atoms of both the alkane-i,j-diyl and the substituent.

The term "biocompatible functional group comprising at least one oxygen atom or two sulphur atoms" refers to two classes of functional groups, wherein one class is a class of oxygen-comprising functional groups and the other class is a class of functional groups comprising or consisting of two sulphur atoms, wherein the functional groups of both classes do not give rise to adverse reactions or side effects if administered to a living organism to be treated with the pharmaceutical composition of the invention or to be diagnosed using the diagnostic composition of the invention. The term "biocompatible" is equivalent to "generally recognized as safe (GRAS)". Means for assessing biocompatibility are well known in the art, include in vitro tests performed on cell lines, in vivo tests on animals as well as clinical tests on human being and do not have to be further detailed here. Any test required or recommended by regulatory authorities for the assessment of whether a compound is generally recognized as safe (GRAS), is preferably employed for identifying those cyclic compounds whose oxygen-containing functional group(s) is/are biocompatible. Preferably the oxygen atom of said biocompatible functional group comprising at least one oxygen atom is available for forming a complex with said protonated primary amino group, said protonated secondary amino group or said protonated guanidinium group. Analogously, preferably one or both of the sulphur atoms of the biocompatible functional group comprising two sulphur atoms is available for complex formation. Preferred biocompatible functional groups comprising at least one oxygen atom include ester (—C(═O)—O—), amide (—C(═O)—NH—), ether (—O—), oxime (—C═N—O—), thioester (—C(═O)—S— as well as —C(═S)—O—), hemiacetal, acetal and sulfoxide (—S(=O)—). More preferred are ester (—C(=O)—O—), amide (—C(=O)—NH—) and ether (—O—). Preferred biocompatible functional groups comprising two sulphur atoms are disulfide (—S—S—) and dithioester (—C(=S)—S—). More preferred is disulfide (—S—S—). Functional groups comprising at least one oxygen atom which are not biocompatible include peroxide.

In a preferred embodiment, all occurrences of A are the same. Alternatively or in addition, all occurrences of B may be the same. If both all occurrences of A are the same, for example a group $A_1$ such as ethane-1,1-diyl and all occurrences of B are the same, for example a group $B_1$ such as methylene, an alternating pattern of building blocks is obtained. The variable p defines the number of repetitions of said pattern within the compound of the invention. Furthermore, A=B may be valid for all occurrences of A and B.

Similarly, all occurrences of X may be the same. Alternatively or in addition, all occurrences of Y may be the same. Furthermore, X=Y may be valid for all occurrences of X and Y.

The lower limit of 3 on the values of p·(n+m) ensures that at least three oxygen atoms are comprised in the compound of the invention. Preferably, at least four oxygen atoms are comprised in the compound of the invention. This may be achieved by a minimal value of p·(n+m) of 4. Preferred ranges of p·(n+m) include 3 to 20, 3 to 10, 4 to 10 and 4 to 8.

It is understood that the words "use of a cyclic compound" also embrace, in addition to uses of one compound, uses of two or more distinct compounds as defined in the main embodiment.

In a preferred embodiment, said compound is selected from a (i) cyclic polyester; (ii) cyclic polyamide; (iii) cyclic polyether; (iv) cyclic polyoxime; (v) polythioester; (vi) polymer of aminoxy acids; (vii) poly-disulfide; and (viii) a cyclic compound belonging to more than one of (i) to (vii). More preferred are cyclic polyesters, cyclic depsipeptides and cyclic polyethers. Yet more preferred are cyclic polyesters.

The present invention also relates to the use of a cyclic (i) polyester, (ii) polyamide, (iii) polyether, (iv) polyoxime, (v) polythioester, (vi) polymer of aminoxy acids, (vii) poly-disulfide, and (viii) a cyclic compound belonging to more than one of (i) to (vii), wherein said cyclic polyester, polyamide, polyether, polyoxime, polythioester, polymer of aminoxy acids, poly-disulfide or compound belonging to more than one of (i) to (vii) is capable of forming a complex with a protonated primary and/or protonated secondary amino group and/or a protonated guanidinium group for the manufacture of a pharmaceutical or diagnostic composition further comprising a pharmaceutically or diagnostically active agent comprising one or more protonated primary and/or protonated secondary amino groups and/or a protonated guanidinium groups, wherein (a) transmembrane and/or transmucosal delivery; (b) solubility in non-aqueous solvents; and/or (c) stability of said active agent are improved.

The term "cyclic" refers to compounds of the invention such as polyesters, polyorthoesters, polyamides, depsipeptides, polyethers and polyoximes of the invention which contain a ring. When used to designate a feature of the compound of the invention as a whole, which is the case here, the term "ring" refers to a ring which includes all functional groups X and Y. The functional group providing closure of said ring may be the same or different from the functional group giving rise to the classification as polyester, polyorthoester, polyamide, depsipeptide, polyoxime or polyether. Preferably, the functional group providing closure is the same as the functional group giving rise to said classification, i.e., in case of a cyclic polyester one further ester linkage is formed when the corresponding linear form is converted into the cyclic form. The term "corresponding linear form" designates a polymer or oligomer (the term "polymer" as used herein includes oligomers) which has a given number of monomers linked together to form a linear polymer, wherein said given number is the same as the number of monomers in the cyclic compound of the invention. In other words, the number of monomers one the one side and on the other side the number of ester functionalities (in case of cyclic polyesters), orthoester functionalities (in case of cyclic polyorthoesters), amide functionalities (in case of cyclic polyamides) or the combined number of ester and amide functionalities (in case of cyclic depsipeptides) are the same.

The term "polymer" is understood to comprise both polymers in the narrow sense, i.e. molecules formed from a plurality of building blocks or one or more than one type (in the latter case said polymers are also referred to as co-polymers), wherein upon formation of the polymer from the building blocks no further molecule(s) such as water is formed, as well as polycondensates, i.e. polymers according to the present invention, wherein upon formation of the polymer from its building blocks (a) further molecule(s) such as water is/are formed in addition to the polymer.

The term "polyester" as used herein relates to compounds which comprise at least two ester functionalities, i.e. two —C(=O)—O— groups. Cyclic esters are also referred to as lactones. The building blocks of polyesters and depsipeptides (see below) are or include, respectively, hydroxy acids. Preferred building blocks or monomers according to the invention are alpha-hydroxy acids and beta-hydroxy acids. Also preferred are hydroxy acids with up to ten carbon atoms, wherein any number below ten is explicitly included in the scope of the invention. As such, preferred alpha-hydroxy acids include alpha-hydroxy acids with two, three, four, five, six, seven, eight, nine or ten carbon atoms or up to 20 carbon atoms. Preferred beta-hydroxy acids include beta-hydroxy acids with three, four, five, six, seven, eight and nine carbon atoms. Specific preferred alpha-hydroxy acids are glycolic acid, lactic acid, alpha-hydroxy n-butyric acid, alpha-hydroxy n-pentanoic acid and alpha-hydroxy n-hexanoic acid. Preferred beta-hydroxy acids include beta-hydroxy propionic acid, beta-hydroxy n-butyric acid, beta-hydroxy n-pentanoic acid and beta-hydroxy n-hexanoic acid. Also envisaged are hydroxy acids with branched alkyl side chains such as beta-hydroxy i-butyric acid and alpha-hydroxy i-pentanoic acid, as well as hydroxy acids with with hydroxyalkyl side chain. Preferably, said hydroxyalkyl side chain carries a terminal hydroxy group. Such cyclic polyesters, polyorthoesters, polyamides, depsipeptides, polyethers and polyoximes of the invention may carry one or more free hydroxyl moieties on the side chain for further exploitation such as derivatization by esterification. Furthermore envisaged are hydroxy acids with aromatic side chains. Hydroxy acids with aromatic side chains include any of the above mentioned aliphatic acids, wherein said acids are substituted with a phenyl group. The phenyl group in turn may be substituted. An example is 2-Phenyl-2-hydroxyacetic acid (mandelic acid). Cyclic polyesters according to the invention may consist of one type of monomer or a plurality of types of monomers. Said plurality may, for example, be a plurality of alpha-hydroxy acids or a mixture of alpha-hydroxy acids and beta-hydroxy acids. In a preferred embodiment, alpha-hydroxy acids and beta-hydroxy acids alternate.

It is understood that polyesters may arise from polymerization of hydroxy acids. Alternatively, polyesters may arise from polymerization of a di-alcohol with a di-acid. The same applies mutatis mutandis to polyamides and depsipeptides of the invention.

The term "orthoester" as used herein relates to compounds comprising a carbon atom linked to three alkoxy groups. Accordingly, polyorthoesters are compounds comprising at least two such functionalities. Cyclic polyorthoesters are valence tautomers of cyclic polyesters (see McGeary and Bruget (2000)). Both tautomeric forms are suitable to practice the present invention. It is furthermore understood that the term "polyorthoester" is to be subsumed under the term "polyester" of the invention.

The term "polythioester" according to the invention refers to compounds comprising at least two thioester functionalities, i.e., (i) at least two —C(=O)—S— groups, (ii) at least two —C(=S)—O— groups, or (iii) at least one —C(=O)—S— group and at least one —C(=S)—O— group.

Also envisaged are cyclic compounds of the invention which are cyclic poly-dithio-esters. The term "poly-dithio-ester" as used herein refers to compounds comprising at least two dithioester functional groups (—C(=S)—S—).

The term "polyamide" according to the invention refers to compounds comprising at least two amide functionalities, i.e. two —C(=O)—NH— groups. Cyclic amides are also designated lactames. The amide bond is also referred to as peptide bond, in particular in the context of peptides. Preferred building blocks or monomers of cyclic polyamides according to the invention are alpha-amino acids and beta-amino acids. Also depsipeptides (see below) comprise alpha-amino acids. Further preferred are amino acids with up to ten carbon atoms, wherein any number below ten is explicitly included in the scope of the invention. As such, preferred alpha-amino acids include alpha-amino acids with two, three, four, five, six, seven, eight, nine or ten carbon atoms. Preferred beta-amino acids include beta-amino acids with three, four, five, six, seven, eight and nine carbon atoms. Specific preferred alpha-amino acids are the naturally occurring amino acids. Particularly preferred alpha-amino acids are Gly, Ala, Val, Leu, Ile, Met and Phe. The occurrence of one or more of the remainder of the naturally occurring amino acids (such as Cys, Asn, Gln, Pro Ser, Thr, Trp, Tyr), where appropriate, is also deliberately envisaged. Further alpha-amino acids are alpha-amino butyric acid and alpha-amino i-butyric acid. Preferred beta-amino acids include beta-alanine. Furthermore, gamma-amino butyric acid may be used as the only or one of the monomers in the cyclic polyamides or depsipeptides of the invention. Cyclic polyamides according to the invention may consist of one type of monomer or a plurality of types of monomers. Said plurality may, for example, be a plurality of alpha-amino acids or a mixture of alpha-amino acids and beta-amino acids. In a preferred embodiment, alpha-amino acids and beta-amino acids alternate.

The term "polyamide" includes also compounds of the invention the monomers of which are alpha and beta aminooxy acids (see, for example, Yang et.al. *J. Am. Chem. Soc.*, 2002, 124, 12410-12411) and related compounds.

The term "depsipeptide" is known in the art and designates herein compounds which comprise or consist of alpha-hydroxy acids and alpha-amino acids, which are linked to each other by ester linkages between the hydroxy group of an alpha-hydroxy acid and the carboxyl group of either a hydroxy acid or an amino acid as well as by amid linkages between the amino group of an alpha-amino acid and the carboxyl group of either a hydroxy acid or an amino acid. More than one type of alpha-hydroxy acid and/or alpha-amino acid may be present in a depsipeptide. On the other hand, also depsipeptides, wherein only one type of alpha-hydroxy acid and/or only one type of alpha-amino acid occurs, are include in the scope of the invention. Alpha-hydroxy acid monomers and alpha-amino acid monomers may alternate. A strictly alternating sequence would imply an even number of monomers in the cyclic depsipeptide of the invention. Alternatively, one or more ester-linked stretches consisting of a plurality (such as two, three, four, five, six, seven, eight, nine or more) of alpha-hydroxy acid monomers may be followed by one or more amid-linked stretches consisting of a plurality (such as two, three, four, five, six, seven, eight, nine or more) of alpha-amino acids. Preferred alpha-amino acids and alpha-hydroxy acids are described herein above.

The term "polyether" refers to compounds comprising at least two ether functional groups. An ether functional groups is represented by —O—, wherein the carbons directly adjacent to the oxygen atom are not substituted by heteroatoms. For example, biocompatible polymers like PEGs are to be subsumed under the term "polyether".

The term "polyoxime" refers to compounds comprising at least two oxime functional groups (—C=N—O—). An exemplary cyclic polyoxime is shown in FIG. 2.

A further preferred class of cyclic compounds of the invention are cyclic polymers of aminoxy acids, preferably of alpha-aminoxy acids. The oxygen-containing functional group in cyclic polymers of aminoxy acids is —C(=O)—NH—O— or —C(=O)—N(OH)—. Polymers of aminoxy acids wherein the functional group is —C(=O)—N(OH)— are also referred to as polyhydroxamic acids.

Another preferred class of cyclic compounds of the invention are cyclic poly-disulfides. The term "poly-disulfide" as used herein refers to compounds comprising at least two disulfide functional groups (—S—S—). An Example is shown in FIG. 2. Disulfides are known to be reversible/breakable under physiological conditions in vivo by reducing agents naturally occurring in the human or animal body such as glutathione and other endogenous mercaptans.

The terms "polyester", "polyamide", "polyether", "polyoxime" and "cyclic polymer of aminoxy acids" include compounds of the invention wherein for all occurrences X=Y=ester (in case of polyester), for all occurrences X=Y=amide (in case of polyamide) etc. Also included are compounds wherein a majority, i.e. more than 50% of all occurrences of X and Y together, are ester (in case of polyester), amide (in case of polyamide), ether (in case of polyether) or oxime (in case of polyoxime), respectively. Accordingly, also included are compounds wherein out of a total of k functional groups (X, Y), k-1 functional groups are of one particular type such as ester, and one functional group is of a different type such as amide. In other words, a preferred class of cyclic compounds of the invention are cyclic polyesters where a single amide bond replaces a single ester bond generating a mono-amide cyclic polyester; In a further preferred embodiment, the cyclic polyester is composed by alpha-hydroxy acids and a single amide bond (CO—NH—) replaces only one ester bond (CO—O—). In a further preferred embodiment, the cyclic polyester is composed of alpha-hydroxy acids and a single amino acid is used to replace a single alpha-hydroxy acid. Such class of cyclic compounds, maintaining the main features of the all polyester bonds cyclic structure, can be synthesized and produced more easily with superior yields. Another example of this type of cyclic compound are mono-oxo crown ethers such as the compound shown in FIG. 2, bottom, right. Such compounds have k-1 ether groups and one ester group.

The term "cyclic compound belonging to more than one of (i) to (vii)" includes poly-ester-co-ethers, depsipeptides, poly-ester-co-oximes, poly-amide-co-esters and the like. A preferred embodiment of said cyclic compound belonging to more than one of (i) to (iv)" are Peg-polyesters (also referred to as oxo-PEGS including mono-oxo PEG and di-oxo PEG, see also FIG. 2): In such embodiment at least two oligomers comprising or consisting of a Peg or a polyether, said Peg or polyether, respectively, having at the two ends a hydroxyl group and a carboxylic acid, are fused together in a single cyclic structure by forming at least two esters bonds (cyclic poly-ether-co-ester). An example of such a cyclic compound can be found in patent application JP55143981 (OKAHARA MITSUO; MATSUSHIMA KENJI) (see also K. Matsushima, N. Kawamura, Y. Nakatsuji and M. Okahara, (1982), Bull. Chem. Soc. Jpn, 55, 2181-2185). In a further preferred embodiment, the cyclic compound of the invention is a cyclic compound belonging to more than one of polyester, polyamide, polyether, polyoxime and cyclic polymer of aminoxy acids. In this embodiment, one or more occurrences of X or Y is —C(=O)—NH—O—.

It is understood that preferred monomers of the polyesters, polyamides, polyethers, polyoximes and cyclic compound belonging to more than one of (i) to (vii) as defined herein above, i.e., preferred hydroxy acids, preferred amino acids and the like, at the same time provide a definition of preferred building blocks A, B of the main embodiment. By removing the hydroxy and the carboxylic acid group from a hydroxy acid disclosed above, an alkane-i,j-diyl is obtained, wherein positions i and j are the positions of the hydroxy and the carboxylic acid group. Similarly, by removing the amino and the carboxylic acid group from a amino acid disclosed above, an alkane-i,j-diyl is obtained, wherein positions i and j are the positions of the amino and the carboxylic acid group. In general, by removing those functional groups present on said monomers which give rise to the functional groups designated X, Y in the main embodiment (for example, —OH and —COOH give rise to —C(=O)—O—; —NH2 and —COOH give rise to —C(=O)—NH—), said alkane-i,j-diyl is obtained. The obtained alkane-i,j-diyl provides a building block A or B which may be bound to any biocompatible oxygen-containing functional group X or Y within the cyclic compound of the invention. It is furthermore understood, that, in line with the main embodiment, said alkane-i,j-diyl may comprise one or more double bonds, may be substituted as defined above, and/or may comprise a cycle as defined above.

The terms "complex" and "complexation" are well known in the art and refer to a reversible association of molecules, atoms, or ions through non-covalent chemical bonds. Usually two interaction partners, a complexing agent having a plurality of functional groups and a small molecule, atom or ion bound by said plurality of functional groups are implied. As used herein, the term complex is not confined to metal ions bound to a complexing agent. It relates in general to complexes between a compound of the invention and a cation or cationic group. The cyclic compounds of the invention provide oxygen-containing functional groups, the oxygen being available for complex formation. An example of an oxygen atom is the ether oxygen in the cyclic polyethers of the invention. The cyclic polyesters, polyamides and, depsipeptides of the invention provide carbonyl groups (which are part of the amide and ester functionalities) as functional groups involved in complex formation. The cyclic polyorthoesters of the invention provide oxygen atoms (which are part of the alkoxy groups in said polyorthoesters) as functional groups involved in complex formation.

It turns out that the advantageous effects of the present invention, i.e., improvement of transmembrane and/or transmucosal delivery, of solubility in non-aqueous solvents, and/ or of stability of the active agents being complexed with the cyclic compound of the invention are not only observed with active agents which are small molecules, but also with active agents which are peptides, polypeptides or proteins. This is particularly surprising, since entirely different mechanisms or effects are responsible for said improvement in either case. In case of small molecules, complexation with cyclic compounds of the invention typically leads to a substantial shielding of said small molecule. This is because size-wise, it is a small molecule (the cyclic compound) complexing another small molecule (the pharmaceutically active agent). In addition, small molecules, due to their small size (for example in the range of 500 Dalton or less) can also be absorbed through a paracellular mechanism, i.e., through the small pores or channels between the cells composing the tissue. If furthermore the small molecule in matter possesses other specific features including a pronounced hydrophobicity, the molecule is absorbed via a transcellular pathway, i.e., by passive absorption, as well. In addition, it has to be understood that any properties, in particular physico-chemical properties of said small molecule, said properties compromising for example transmembrane and/or transmucosal delivery, become less relevant upon complexation, since complexation entails shielding of essentially the entire small molecule due to size similarity.

In case of biopolymers such as for example peptides, polypeptides or proteins on the other hand, shielding of the entire molecule by the cyclic compound of the invention typically does not occur since in general the size of a polypeptide or protein will exceed significantly the size of said cyclic compound; nevertheless, said improvement does still occur. Surprisingly it turns out that unlike small molecules that are known to cross membranes, the local shielding of charges on said peptides, polypeptides or proteins, which on the contrary are known not to cross membranes, is sufficient to entail said improvement. A global shielding of the entire peptide, polypeptide or protein surprisingly turns out to not the major driving force when said improvement is to be achieved.

Uses and methods of the invention may be effected by using a mixture of cyclic compounds selected from more than one class of compounds such as polyesters, polyorthoesters, polyamides, depsipeptides, polyethers and polyoximes. Alternatively, only compounds of one particular class such as only cyclic polyesters or only cyclic polyorthoesters or only cyclic polyamides or only cyclic depsipeptides or only cyclic polyethers or only cyclic polyoximes may be used. If this is the case, for example, said polyesters may be mixtures of distinct polyesters, said polyorthoesters may be mixtures of distinct polyorthoesters, said polyamides may be mixtures of distinct polyamides and said depsipeptides may be mixtures of distinct depsipeptides. Preferably, only one chemical species, i.e. a specific polyester, a specific polyorthoester, a specific polyamide or a specific depsipeptide is used.

The capability of the compounds of the invention to form a complex with said protonated primary amino group or protonated secondary amino group or protonated guanidinium group can be determined in a straightforward manner by the skilled person.

A suitable assay comprises assessment of the solubility of an active agent such as a peptide or protein, for example insulin or erythropoietin, in organic solvent, for example methanol, ethanol or dichloromethan. In a first experiment, solubility of the peptide or protein in the organic solvent is determined. In a second experiment, a three to ten-fold molar excess, more preferably three- to five-fold molar excess of a compound of the invention such as a cyclic polyester, polyorthoester, polyamide, depsipeptide, polyether or polyoxime is added to the peptide or protein together with the organic solvent. The term "molar excess" refers to an amount of the cyclic compound which exceeds the amount of protonated primary amino groups, protonated secondary amino groups and protonated guanidinium groups of the peptide or protein. In the absence of a cyclic compound of the invention, the peptide/protein generates a suspension, colloidal suspension or deposits in the form of particles. The same applies to a mixture of said peptide or protein with cyclic compounds which are not capable of forming a complex with a protonated primary and/or protonated secondary amino group and/or a protonated guanidinium group. On the other hand, a cyclic compound capable of forming a complex with a protonated primary and/or protonated secondary amino group and/or a protonated guanidinium group generates a clear solution of the peptide/protein in the organic solvent.

In a further embodiment of the assay, any insoluble material still present in either experiment may be removed by centrifugation and the concentration of peptide/protein in solution subsequently determined by means known in the art. Such means include HPLC analysis of the supernatant from the centrifugation and determination of the amount of peptide or protein by determining the area of the peptide/protein peak in the chromatogram.

Preferably, the dissociation constant $K_D$ of said complex is less $10^{-3}$, more preferred less than $10^{-4}$, $10^{-5}$ or $10^{-6}$.

The term "pharmaceutically active agent" refers to any agent capable of eliciting pharmaceutical effects. The term "drug" is used equivalently herein. A pharmaceutical composition according to the invention may comprise one or more pharmaceutically active agents. Preferred pharmaceutically active agents are peptides, polypeptides, proteins, antibodies and small molecules, in particular small organic molecules. The term "(poly)peptide" is used herein to designate both peptides and polypeptides. Also included are pharmaceutically active agents which are (poly)saccharides or nucleic acids. Preferred polysaccharides are polysaccharides having one or more sulfonic acid groups ($-SO_3^-$) such as heparin which is further discussed below. In case of pharmaceutically active agents being nucleic acids it is envisaged to use the cyclic compounds for the shielding of the positive charges of counterions of the negatively charged phosphates. Said (positively charged) counterions include ammonium, amino acids such as Lys and derivatives thereof, and metal ions. Also included are nucleic acids where the phosphate is esterified with an alkyl amino or alkyl guanidino group. Nucleic acids in accordance with the present invention, include DNA, such as cDNA or genomic DNA, and RNA. It is understood that the term "RNA" as used herein comprises all forms of RNA including mRNA, ncRNA (non-coding RNA), tRNA and rRNA. The term "non-coding RNA" includes siRNA (small interfering RNA), miRNA (micro RNA), rasiRNA (repeat associated RNA), snoRNA (small nucleolar RNA), and snRNA (small nuclear RNA).

A preferred nucleic acid is a small interfering RNA. The term "small interfering RNA" (siRNA), sometimes known as short interfering RNA or silencing RNA, refers to a class of generally short and double-stranded RNA molecules that play a variety of roles in biology and, to an increasing extent, in treatment of a variety of diseases and conditions. Most notably, siRNA is involved in the RNA interference (RNAi) pathway where the siRNA interferes with the expression of a specific gene (see, e.g. Zamore Nat Struct Biol 2001, 8(9): 746-50; Tuschl T. CHEMBIOCHEM. 2001, 2:239-245; Scherr and Eder, Cell Cycle. 2007 February; 6(4):444-9; Leung and Whittaker, Pharmacol Ther. 2005 August; 107(2): 222-39; de Fougerolles et al., Nat. Rev. Drug Discov. 2007, 6: 443-453).

The term "diagnostically active agent" refers to any agent suitable for practising a method of diagnosis. Examples include peptides, polypeptides, antibodies or small organic molecules which bind a target molecule presence, absence or amount of which is to be determined. The target molecule in turn may be any molecule occurring in the human or animal body in a healthy and/or diseased state. The term "target molecule" includes peptides, polypeptides and proteins. Preferably, said diagnostically active agent is detectably labelled.

The term "antibody" includes monoclonal antibodies, polyclonal antibodies, single chain antibodies, or fragments thereof, also including bispecific antibodies, synthetic antibodies, antibody fragments, such as Fab, a $F(ab_2)'$, Fv or scFv fragments etc., or a chemically modified derivative of any of these. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning: A Laboratory Manual, Cold Spring Harbor Laboratory, Cold Spring Harbor, N.Y., 1989.

The term "monoclonal" or "polyclonal antibody" (see Harlow and Lane, (1988), loc. cit.) also relates to derivatives of said antibodies which retain or essentially retain their binding specificity.

The term "scFv fragment" (single-chain Fv fragment) is well understood in the art and preferred due to its small size and the possibility to recombinantly produce such fragments.

In a particularly preferred embodiment of the use or the method of the invention, said antibody or antibody binding portion is or is derived from a human antibody or a humanized antibody.

The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861.

The term "small molecule" as used herein includes the agents listed in the following, wherein the corresponding medical indication is also provided: (a) Synthetic and natural Antibiotics: derivatives of Pyridonic ring (Nalidixix acid, Oxolinic acid), Penicillin derivatives (Benzyl-Penicillin, Phenoxymethyl-penicillin, Meticillin, Oxacillin, Ampicillin, Amoxycillin, Pivampicillin, Talampicillin, Carbenicillin, Ticarcillin) Cefalosporin derivatives (Cefalosporin C, Cefaloglycine, Cefotaxime, Cefmetazole, Cefradin, Cefalexin, Cefalotin, Cefaloridin, Cefazolin, Cefsulodin, Cefacetril, Cefapyrin, Cefuroxime, Cefamandol, Cefoxitin, Cefazol Cefoperazone, Ceftriaxone) Antibiotics aminoglycosides (Streptomycin, Neomycin, Gentamicin, Tobramycin, Amikacin), Polyenes (Nistatin, Amphotericin B), Anti-Tubercolosis (Para-amino salicylic acid) (b) Neuro-transmitters: Catecholamines (Adrenaline, Noradrenaline, L-Dopamine, Dopamine, Carbidopa) Serotonin, γ-amino-butyric acid (GABA); (c) Anti-inflammatory and Analgesic non steroids: Salicylic Acid, Acethylsalicylic acid; Phenylacetic acids: Ibuprofen, Phenoxyprofen, Ketoprofen, Naproxen, Diclofenac; Etherocyclic acetic acids: Indomethacine, Clometacine, Sulindac, Zomepirac, Thiapropheic acid; Antranilic acids: Mephenamic acid, Fluphenamic acid, Meclophenamic acid, Tolphenamic acid, Niflumic acid. (d) Anti-coagulants: Heparin (either sodium or calcium derivatives), Dermatan Sulfate, Enoxaparin Sodium, Dalteparin Sodium.; (e) Diuretics: Furosemide, Bumetanide, Etacrinic acid, Tienilic acid, Triamterene, Amiloride,; (e) Variuos: Valproic acid (anti-epilectic), Clavulanic acid (inhibitor of β-Lactamases), Lithium salts (anti-Psychotic).

It is understood that the invention also relates to further therapeutically relevant small molecules which are modified according to uses and methods of the invention, i.e. by complex formation. In this case, the envisaged medical indication is the indication which can be prevented, ameliorated or cured with the small molecule under consideration.

The term "peptide" according to the present invention and associated diseases to be treated include: (a) the peptide is Lisinopril also known as Privinil and the disease is hypertension; (b); the peptide is Goserelin, synthetic decapeptide analogue of luteinizing hormone-releasing hormone (LHRH) and the disease is Prostate Cancer; (c) the peptide is Calcitonin and the disease is Osteoporosis; (d) the peptide is Leuprolide and the disease is Prostate Cancer; (e) the peptide is Glucagon the disease is hypoglycemia; (f) the peptide is Integrilin the disease is Anti-coagulation; (g) the peptide is hirudin and is used as anticoagulant and antithrombotic agent, (h) the peptide is desmopressin, which is an analogue of vasopressin and is used therapeutically as an antidiuretic and in the management of bleeding in individuals with some forms of hemophilia and von Willebrand's disease, and wherein the (poly)peptide is modified as defined herein above, i.e. by formation of a complex with cyclic compounds of the invention.

It is understood that the invention also relates to the use of further therapeutically relevant peptides which are modified (i.e. complexed) according to the invention. In this case, the envisaged medical indication is the indication which can be prevented, ameliorated or cured with the peptide or polypeptide under consideration.

The term "(poly)peptide" according to the present invention and associated diseases to be treated include: (a) the (poly)peptide is insulin (Including Insulin Lispro, insulin aspart, and the disease is diabetes; (b) the (poly)peptide is Epoietin alpha and the disease is anemia; (c) the (poly)peptide is Epoietin beta and the disease is anemia; (d) the (poly) peptide is darbepoetin and the disease is anemia; (e) the (poly)peptide is Erythropoietin and the disease is anemia or chronic renal failure; (f) the (poly)peptide is Filgrastim and the indications are Immune disorders, leukemia, diabetic foot ulcers; Leukopenia, and neoplastic diseases; (g) the (poly) peptide is Lenograstim and the indication is Leukopenia; (h) the (poly)peptide is Sargramostin and the indication is Leukopenia; (i) the (poly)peptide is Molgramostin and the indication is Leukopenia; (j) the (poly)peptide is Mirimostim and the indication is Leukopenia; (k) the (poly)peptide is Nartograstim and the indication is Leukopenia; (l) the (poly) peptide is GCSF and the disease is Chemotherapy induced neutropenia; (m) the (poly)peptide is GMCSF and the indication is Autologous bone marrow transplant; (n) the (poly) peptide is an asparaginase and the disease is cancer; Preferred cancer forms amenable to treatment with asparaginases are lymphoblastic leukemias and large cell lymphoma; (o) the (poly)peptide is Factor Vila, Factor VIII, Factor IX products (Blood clotting factors) and the disease are Hemophilia A, Hemophilia b; (p) the (poly)peptide is interferon a -alpha- (includes interferon alpha-2a, interferon alpha-2b, interferon alfacon-1, interferon alpha 3n) and the disease is chronic hepatitis B or C and some types of cancer; (q) the (poly) peptide is interferon β (wherein -beta- includes Interferon beta-1a, and interferon beta 1b) to treat Multiple Sclerosis and hepatitis; (r) the (poly)peptide is interferon γ (wherein -gamma- includes Interferon gamma-1b) and the disease is fibrosis, tuberculosis, meningitis or cancer; (s) the (poly) peptide is human growth hormone (hGH) and the disease is Human growth deficiency in children; (t) the (poly)peptide is somatrem/somatropin and the disease is growth hormone deficiency in children; (u) the (poly)peptide is a superoxide dismutase and the disease is a brain injury; (v) the (poly) peptide is interleukine-2 and the disease is cancer (metastatic renal cancer) or a condition requiring immunostimulation; (w) The human growth hormone (hGH) antagonist B2036 is well known in the art. B2036 is obtained from hGH by the introduction of nine amino acid replacements conferring antagonistic properties and increased receptor affinity (see U.S. Pat. No. 5,849,535). For the purpose of treating acromegaly any other growth hormone (GH)-receptor antagonist (alternatively or in addition to the GH-receptor antagonist B2036) is envisaged; (x) the (poly)peptide is Transtuzumab and the disease is Cancer. It is understood that the term (poly)peptide as used herein includes peptides, polypeptides and proteins.

It is understood that the invention also relates to the use of further therapeutically relevant (poly)peptides which are modified (i.e complexed) according to the invention. In this case, the envisaged medical indication is the indication which can be prevented, ameliorated or cured with the (poly)peptide under consideration.

The pharmaceutically or diagnostically active agent according to the invention exhibits one or more groups selected from protonated primary amino groups ($-NH_3^+$), protonated secondary amino groups ($-NH_2^+-$) and protonated guanidinium groups ($-NH-C(=NH_2^+)-NH_2$). As further detailed below, the presence of one or more positive charges limits the possibilities to formulate and deliver said agent. In a preferred embodiment, said primary or said secondary amino group is a primary or secondary aliphatic amino group, respectively. Also, said guanidinium group is preferably an aliphatic guanidinium group, i.e. a guanidinium group attached to an aliphatic moiety. In those cases where said active agent is a peptide, polypeptide, protein or antibody, it is understood that "primary aliphatic amino group" includes or refers to the amino group of Lys, and "aliphatic guanidinium group" includes or refers to the guanidinium group of Arg.

In addition to pharmaceutically or diagnostically active agents, constituents of functional food or food supplements may be complexed with the compounds of the invention, provided that the constituent of a functional food or the constituent of a food supplement carries one or more of protonated primary amino groups, protonated secondary amino groups and protonated guanidinium groups. Such constituent (also referred to as active agent) may take the place of the pharmaceutically or diagnostically active agents in the uses and methods of the invention. An example of a constituents of functional food is creatine.

Accordingly, the present invention also relates to use of a cyclic compound as defined in the main embodiment; wherein said cyclic compound is capable of forming a complex with a protonated primary and/or protonated secondary amino group and/or a protonated guanidinium group for improving (a) transmembrane and/or transmucosal delivery; (b) solubility in non-aqueous solvents; and/or (c) stability of an active agent, wherein said active agent comprises one or more protonated primary and/or protonated secondary amino groups and/or a protonated guanidinium groups.

The term active agent comprises pharmaceutically active agents or drugs, diagnostically active agents as well as constituents of functional food and constituents of food supplements.

The pharmaceutical composition may further comprise pharmaceutically acceptable carriers, excipients and/or diluents. Examples of suitable pharmaceutical carriers, excipients and/or diluents are well known in the art and include phosphate buffered saline solutions, water, emulsions, such as oil/water emulsions, various types of wetting agents, sterile solutions etc. Preferred carriers for transmembrane or transmucosal delivery or diluents for formulation according to the invention include the non-aqueous solvents further discussed below. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg/kg body weight per dose; however, doses below or above this exemplary range are envisioned, especially considering the aforementioned factors. Envisaged formulations furthermore comprise microspheres, liposomes, microcapsules, and nanoparticles/nanocapsules.

Additional envisaged constituents of the pharmaceutical or diagnostic compositions according to the invention include cyclodextrins (see, for example, Irie and Uekama (1999) or Challa et al. (2005)) and/or chitosan. Cyclodextrins form inclusion complexes with hydrophobic moieties present on a compound. Furthermore, they present a hydrophilic exterior surface. Compositions comprising cyclodextrins or chitosan may exhibit retard characteristics, i.e., they provide for a delayed release and/or a release over an extended period of time of the active agent.

Accordingly, in another preferred embodiment, said pharmaceutical or diagnostic composition to be manufactured further comprises a cyclodextrins. Cyclodextrins are known in the art and include alpha-cyclodextrin, beta-cyclodextrin and gamma-cyclodextrin. In other words, the active agent is in a first step complexed with cyclic compounds of the invention such as cyclic polyesters, polyorthoesters, polyamides, depsipeptides, polyethers and/or polyoximes that shield the positive charge(s) present on the active agent and then, in second step, the active agent is complexed, to form a second layer, with cyclodextrines, more specifically be the hydrohphobic inner cavity of cyclodextrins, thereby generating in total two levels of complexations. This opens possibilities to design novel delivery approaches: for examples, entrapping the active ingredient into (i) liposomes, (ii) microspheres, (iii) microcapsules, (iv) Nanoparticles/nanocapsules.

To explain further, the increase of hydrophobicity and the shielding of the positive charge(s) present on the pharmaceutically or diagnostically active agent opens previously unavailable possibilities for delivery, by making use of and enhancing currently available delivery systems. For example, cyclodextrines are known to have lipophilic inner cavities and hydrophilic outer surfaces and are capable of interacting with a large number of molecules. Cyclodextrines are used in formulation to improve apparent drug solubility of hydrophobic (poorly water-soluble) drugs and thus enhance the bioavailability of insoluble drugs by increasing drug solubility, dissolution, and or drug permeability. In the context of the present invention, the enhanced hydrophobicity of the active agent due to the shielding of the positive charge(s) by cyclic compounds of the invention allows more direct and deeper incorporation into the lipophilic core of the cyclodextrine structure. In other words, a hydrophilic active agent being non covalently and temporarily complexed with compounds of the invention, such as cyclic polyesters, polyorthoesters, polyamides, depsipeptides and/or polyethers, changes its biophysical properties and becomes hydrophobic such that it—or hydrophobic parts of if—can insert into the inner part (lipophilic core) of cyclodextrins. As a result, the active agent is complexed first with cyclic compounds of the invention that shield the positive charge(s) present and then, in a second step, the complex formed by the active agent and said cyclic compound(s) is allowed to form a complex with one or more cyclodextrins, thereby yielding in total two layers of complexation. The double complex is expected to be suitable for non-invasive drug delivery, including ocular, rectal, dermal and transdermal delivery, furthermore in parenteral drug delivery (injections), to target brain delivery by enhancing blood-brain barrier (BBB) passage, and in controlled drug delivery to act as functional carrier materials in pharmaceutical formulation to obtain efficient and precise delivery.

Furthermore, the increase of hydrophobicity by the shielding of the positive charge(s) present on the pharmaceutically or diagnostically active agent according to the uses and methods of the present invention opens possibilities to design novel delivery approaches: for example, entrapping the active ingredient into (i) liposomes, (ii) microspheres, (iii) Microcapsules, (iv) nanoparticles/nanocapsules composed of, for example, but not limited to, polyacrylic acids (PAA), polymethacrylic acids (PMAA), polylactic and glycolic acids (PLGA), gabexate mesylate (GM), chitosan, starch, Terephthaloyl chloride (TC), crosslinked cyclodextrines, poly(ethylcyanoacrilate) (PECA), PEGs, and the like.

The term "transmembrane delivery" relates to the capability of said active agent to cross cell membranes. Since cell membranes comprise a hydrophobic layer formed by the lipophilic parts of membrane lipids, charged molecules do not readily cross the membrane. As a consequence, delivery across membranes is negligible or zero. It is understood that an improvement of the transmembrane delivery also entails an improvement of transdermal delivery and transepithelial delivery.

The term "transmucosal delivery" relates to the capability of said active agent to cross the mucosa. Any mucosa is envisaged, including the mucosa of mouse, nose and lungs. Since any mucosa comprises cell membranes, the considerations relating to cell membranes above apply to mucosa as well.

The term "improved solubility" refers to any increase of solubility in said non-aqueous solvent. Preferably, the increase in solubility is 1,2-fold; 1,5-fold, twofold, threefold, fourfold, fivefold, tenfold, hundredfold or thousandfold. Also increases in solubility by more than three orders of magnitude are deliberately envisaged.

The term "non-aqueous solvent" as used herein relates to solvents which are not on an aqueous basis. The term includes organic solvents, in particular apolar organic solvents, organic solvents with a smaller dipole moment than water as well as organic solvents which are hydrophobic, i.e. solvents which are hardly or not at all miscible with water. The term "organic solvent" is known in the art and relates to carbon-based substances commonly used in the chemical industry, capable of dissolving or dispersing one or more substances. Generally speaking, organic solvents are more lipophilic or hydrophobic than water. As a consequence, their logP values are generally greater than zero. Organic solvents according to the invention refer to unsubstituted hydrocarbon solvents like paraffinic, aliphatic and aromatic hydrocarbons and their derivatives containing heteratoms, like oxygen (e.g. alcohols, ketones, glycol esters), halogens (e.g. carbon tetrachloride), nitrogen (e.g. DMF, dimethyl formamide and acetonitrile) or sulphur (e.g. DMSO: dimethyl sulfoxide). Commonly used organic solvents are methanol, ethanol, alcohols from $C_3$ to $C_{10}$, acetonitrile, butanone, 1,1,1-trifluoroethane (TFE), hexafluoroisopropanol (HFIP), ethyl acetate, carbon tetra-chloride, butanol, dibutyl ether, diethyl ether, cyclohexane, methylene chloride (dichloromethane), hexane, butyl acetate, di-isopropyl ether, benzene, dipentyl ether, chloroform, heptane, tetrachloroethylene, toluene, hexadecane, dimethylformamide (DMF), tetrahydrofurane (THF) and dioxane.

Preferred non-aqueous solvents according to the invention include solvents which may be used as a constituent in a pharmaceutical or diagnostic composition and/or solvents which may be used during the course of the manufacture and formulation of said pharmaceutical or diagnostic composition. In other words, the medical use of such solvents is approved and/or their use does not pose a threaten to the health of an individual to be treated. Specific non-aqueous solvents which are deliberately envisaged include organic solvents described above. The term "non-aqueous solvent" also includes natural products such as oils including olive oil. Another preferred non-aqueous solvent is a FDA approved hydrophobic vehicle or diluent, such as for example, but not limited to Cremofor EL.

The term "stability" includes the shelf life of the active agent in pure form or of formulations comprising the active agent. As such, the term "stability" relates to stability in both solid form (pure complex or solid pharmaceutical or diagnostic composition) of the active agent as well in liquid/solution form (including liquid formulations). It furthermore includes thermostability as well as stability against enzymatic degradation. The term "stability" includes maintenance of biological, pharmaceutical and/or diagnostic activity. The term "stability" also refers to stability of the constituents or functional food or food supplements described herein above. It has to be understood that improvement of stability of said active agent is not an obvious consequence of or extrapolation from an improvement of transmembrane or transmucosal delivery. In fact, for the improvement of stability the modulation by the cyclic compound of the interaction between molecules of the active agent is relevant as opposed to the modulation of the interaction between the active agent and the environment in a membrane or mucosa. This is particularly advantageous for easily degradable active molecules, including nucleic acids.

Furthermore, complexation of pharmaceutically active ingredients with cyclic compounds such as but not limited to crown ethers provides significant advantages in the field of galenics and pharmaceutical techniques. Indeed, especially in the case of biopolymers like for example peptides, polypeptides, proteins and nucleic acids that can be handled mainly in aqueous media, the dual and concomitant option of having a pharmaceutical ingredient be soluble both in water as well as in organic solvents (as a complex with cyclic compounds of the invention) may allow improved galenic forms including but not limited to: pills, tablets, capsules, suppository, elisirs, aereosols, drops, powders, lyophilized, emulsions, gels, creams, patches and colloids It has to be understood that improvement of galenic forms of said active agent is not an obvious consequence of or extrapolation from an improvement of transmembrane or transmucosal delivery. Cyclic compounds according to the invention lead to a increase of the hydrophobicity of a pharmaceutically or diagnostically active agent upon complexation with the cyclic compound. Concomitantly, a shielding of the positive charge of the protonated primary or secondary amino group or protonated guanidinium group occurs. The increase of hydrophobicity and the shielding of the positive charge(s) present on the pharmaceutically or diagnostically active agent opens previously unavailable possibilities for formulation. For example, predominantly hydrophilic active agents such as peptides, polypeptides or proteins including antibodies may be dissolved (in their complexed form) in solvents where their solubility in their uncomplexed form is low or zero. Such solvents include non-aqueous solvents. Furthermore, the increased hydrophobicity of the active agent in its complexed form opens new routes of administration for active agents which up to now could only be administered in an invasive manner such as intravenously. Despite such invasive administration (including intravenous administration) exhibits known disadvantages such as partial or significant degradation of the active agent in the liver, no other options have been available so far for a number of active agents including in particular proteinaceous active agents. Upon complexation with cyclic compounds according to the invention the active agent is rendered sufficiently hydrophobic to ensure sufficient permeation through cell membranes such as the cell membranes present in the mucosa or the skin (see FIG. 1 for illustration). As a consequence, non-invasive delivery routes which are further detailed below can be considered for such active agents. Alternatively, non-invasive delivery may be an option also for the uncomplexed form of the active agent, however, with the disadvantage of limited permeation of the mucosa or the skin. In such a case, complexation with cyclic polyesters, cyclic polyorthoesters, cyclic polyamides, cyclic depsipeptides and polyethers according to the invention enhances delivery and renders non-invasive delivery the preferred route of delivery. The pharmaceutical or diagnostic compositions obtained according to the use of the invention are preferably hydrophobic, noting that the hydrophobic complex of the active agent permits use of hydrophobic carriers. Owing to the hydrophobicity (and lipophilicity) of the composition, release of the active agent upon delivery to the subject may be retarded as compared to a conventional, less hydrophobic formulation. In other words, certain compositions obtained according to the invention are retard forms of the comprised active agent.

In a preferred embodiment, the cyclic compound of the invention has a logP value which is greater than 1, more preferred greater than 2 and yet more preferred greater than 3.

In addition, the stability of active agents may be increased by complexation with cyclic compounds according to the invention.

A further advantage of the present invention relates to invasive delivery, in particular to subcutaneous delivery. The volume of a pharmaceutical or diagnostic composition for subcutaneous delivery is inherently limited. If conventional formulation does not allow to obtain a solution for injection, wherein the limited volume for subcutaneous injection comprises the required dose, treatment is cumbersome (short intervals between administrations) or impossible. Noting that the uses of the invention permit preparation of compositions with elevated concentrations of the active agent, these problems in the prior art may be overcome.

The cyclic compounds such as polyesters, cyclic polyorthoesters, cyclic polyamides, cyclic depsipeptides and cyclic polyethers according to the invention have the further advantage that their interaction (complex formation) with the active agent is transient. The term "transient" as used herein refers to reversibility under physiological conditions. Upon passage of the cell membrane, mucosa and/or skin, the cyclic compounds either detach from the active agent, for example as a consequence of the presence of competing ligands such as ammonium ions or primary or secondary amides, or they are degraded.

Physiological conditions in accordance with the present invention may vary significantly, for example when comparing the interior of a cell to the extracellular space. Exemplary intracellular conditions comprise 14 mM $Na^+$, 140 mM $K^+$, $10^{-7}$ mM $Ca^{2+}$, 20 mM $Mg^{2+}$, 4 mM $Cl^-$, 10 mM $HCO_3^-$, 11 mM $HPO_4^{2-}$ and $H_2PO_4^-$, 1 mM $SO_4^{2-}$, 45 mM phosphocreatine, 14 mM carnosine, 8 mM amino acids, 9 mM creatine, 1.5 mM lactate, 5 mM ATP, 3.7 mM hexose monophosphate, 4 mM protein and 4 mM urea. Exemplary interstitial conditions comprise 140 mM $Na^+$, 4 mM $K^+$, 1.2 mM $Ca^{2+}$, 0.7 mM $Mg^{2+}$, 108 mM $Cl^-$, 28.3 mM $HCO_3^-$, 2 mM $HPO_4^{2-}$ and $H_2PO_4^-$, 0.5 mM $SO_4^{2-}$", 2 mM amino acids, 0.2 mM creatine, 1.2 mM lactate, 5.6 mM glucose, 0.2 mMprotein and 4 mM urea.

The terms "hydrophobic" and "hydrophobicity" are well known in the art and designate a low or none miscibility with water and aqueous media. The terms "lipophilic" and "lipophilicity" are used with equivalent meaning herein. A parameter commonly used to quantify hydrophobicity is the logP value.

The mass flux of a molecule at the interface of two immiscible or substantially immiscible solvents is governed by its lipophilicity. The more lipophilic a molecule is, the more soluble it is in the lipophilic organic phase. The partition coefficient of a molecule that is observed between water and n-octanol has been adopted as the standard measure of lipophilicity. The partition coefficient P of a species A is defined as the ratio $P=[A]_{n-octanol}/[A]_{water}$. A figure commonly reported is the logP value, which is the logarithm of the partition coefficient. In case a molecule is ionizable, a plurality of distinct microspecies (ionized and not ionized forms of the molecule) will in principle be present in both phases. The quantity describing the overall lipophilicity of an ionizable species is the distribution coefficient D, defined as the ratio D=[sum of the concentrations of all microspecies]$_{n-octanol}$/[sum of the concentrations of all microspecies]$_{water}$. Analogous to logP, frequently the logarithm of the distribution coefficient, logD, is reported.

If the lipophilic character of a substituent on a first molecule is to be assessed and/or to be determined quantitatively, one may assess a second molecule corresponding to that substituent, wherein said second molecule is obtained, for example, by breaking the bond connecting said substituent to the remainder of the first molecule and connecting (the) free valence(s) obtained thereby to hydrogen(s).

Alternatively, the contribution of the substituent to the logP of a molecule may be determined. The contribution $\pi_X$ of a substituent X to the logP of a molecule R—X is defined as $\pi_X$=logP$_{R-X}$–logP$_{R-H}$, wherein R—H is the unsubstituted parent compound. Values of P and D greater than one as well as logP, logD and $\pi_X$ values greater than zero indicate lipophilic/hydrophobic character, whereas values of P and D smaller than one as well as logP, logD and $\pi_X$ values smaller than zero indicate hydrophilic character of the respective molecules or substituents.

The above described parameters characterizing the lipophilicity of the lipophilic group according to the invention can be determined by experimental means and/or predicted by computational methods known in the art (see for example Sangster, Octanol-water Partition Coeffcients: fundamentals and physical chemistry, John Wiley & Sons, Chichester. (1997)).

In practice, logP, logD and $\pi_X$ values will vary to a certain extent according to the specific conditions under which they are measured.

It has been shown that for drugs or active agents to have a reasonable probability of being well absorbed their logP value must not be greater than 5. The probability density of logP values of drugs on the market (see, for example, http://www.organic-chemistry.org/prog/peo/cLogP.html) shows a maximum at a logP value around 3.

In a preferred embodiment of the uses and methods (methods are described further below) of the invention, said compound such as said cyclic polyester, polyorthoester, polyamide, depsipeptide, polyether or polyoxime is biodegradable. It further preferred that said compound biocompatible. The term "biodegradable" refers to substances which are degradable in living organisms. The "biocompatible" denotes substances which do not give rise to adverse reactions of the human or animal body, preferably neither in their intact form nor when degraded (for further details regarding the term "biocompatible" see herein above). As discussed herein above, various linear polyesters including poly(lactic), poly (glycolic) and polylactic-co-glycolic) acid (PLGA) have established biodegradable and biocompatible characteristics. It is expected that their corresponding cyclic forms exhibit very similar biodegradable and biocompatible characteristics. Biodegradability may be expressed in quantitative terms for example in terms of the half-life of a cyclic compound of the invention in plasma. Means and methods for determining half-life in plasma are known in the art. An exemplary assay is provided in Example 7 enclosed herewith. In a preferred embodiment, the half-life of a cyclic compound of the invention in plasma is shorter than 4 hours, more preferably shorter than 3 hours, 2 hours, 1 hour, 30 min, 20 min, 10 min or 5 min. The term "biodegradable" refers to degradation of said compound, wherein it is understood that degradation consists of or includes cleavage or hydrolysis of a least one of said functional groups X, Y of said cyclic compound.

Cyclic polyethylenglycol structures (crown ethers) are known to bind cations. The most widely used compound, 18-crown-6, shows a moderate or low toxicity (in mice LD 50 reported is 0.71 g/Kg, see Toxicology and Applied Pharmacology, 1978, 44, 263-268).

Cyclic polyethylenglycols (PEG) with a biodegradable junction permit complexation of cations as well as of primary and secondary amines and guanidinium groups. Cyclic polyethylenglycols with a biodegradable junction are expected to present in vivo negligible or none toxicity due to the physiological degradation under physiological conditions of the cyclic form into the linear isoform. Further examples include the oxo crown ethers, which are known in the literature (*Bull. Chem. Soc. Jpn.*, 1982, 55, 2181-2185) or a sugar based cyclic PEG where the sugar provides the biodegradable unit (for an Example see FIG. 2 enclosed herewith). Further examples of a biodegradable junction include acetals of PEG with a ketone or an aldehyde such as acetaldehyde or formaldehyde.

In an alternative embodiment, the use of polyacrylamides and polyacrylates, for example poly-N-Isopropylacrylamide and butylmethacrylates, is envisaged. These polymers have little or nor biodegradability.

In a further preferred embodiment of the uses and methods of the invention, the complex formation of said compound with said primary and/or secondary protonated amino group and/or protonated guanidinium group is selective. Selectivity can be assessed by the skilled person in a straightforward manner. To this end, assays described herein and used for determining the capability of forming a complex are performed repeatedly (or in parallel), wherein one implementation of the assay is directed to determining the complex formation of said compound with said primary and/or secondary protonated amino group and/or protonated guanidinium group and at least one further implementation of the assay is directed to determining the complex formation of said compound with a competing species. Competing species include metal ions such $K^+$ and $Na^+$. Selectivity means that a majority of said compounds forms a complex with said primary and/or secondary protonated amino group and/or protonated guanidinium group ("complex A"; wherein "complex A" designates the amount or concentration of the complex formed between said cyclic compound on the one side and said primary and/or secondary protonated amino group and/or protonated guanidinium group on the other side), whereas the remainder (or a fraction of the remainder) forms a complex with one or more competing species ("complex B"; wherein "complex B" designates the sum of the amounts or concentrations of the complexes with the competing species). In other words, the ratio complex A/complex B is greater than 1. Preferably, said ratio is 1,2; 1,5; 2; 3; 4; 5; 10; 100, 1000 or more.

In a further preferred embodiment of the uses and methods of the invention, a counter ion is added to the composition. Preferred counter ions for a pharmaceutically or diagnostically active agent comprising one or more protonated primary and/or secondary amino groups and/or one or more protonated guanidinium groups, in particular for peptides, polypeptides and proteins, include trifluouracetate (TFA) and salts of alkanoic acids, preferably of alkanoic acids having between 2 and 30, more preferred between 2 and 20, yet more preferred between 2 and 10 carbon atoms. In other preferred embodiments such counter ion may comprise an aromatic group. These counter ions may be used to replace other counter ions forming a salt with said primary and/or secondary protonated amino group and/or protonated guanidinium group. Salts of alkanoic acids are more lipophilic than the generally occurring counter ions such as phosphate. TFA furthermore exhibits a lower pKa value, the consequence being a stronger salt link between the primary or secondary protonated amino group or protonated guanidinium group on the one side and TFA on the other side. Aryl carboxylates are further examples of suitable counterions. Another preferred class of counter ions in particular for peptides, polypeptides and proteins are alkyl or aryl sulfonic acids. Preferred alkyl sulfonic acids have an alkyl chain with between 2 and 30, more preferred between 8 and 10 carbon atoms. Aryl sulfonic acids with one or more alkyl substituents on the aromatic ring, each alkyl substituent preferably having between 2 and 30, more preferred between 8 and 10 carbon atoms, are further examples of suitable counterions. Another class of preferred counter ions, in particular for peptides, polypeptides and proteins, are phospholipids with at least an acidic proton on the phosphate, such as a phosphatidyl glycerol or phosphatidyl sugar with one acidic proton, or a phosphatidic acid with two acidic protons. The alkanoic acids comprised in said phospholipids or the phosphatidyl moieties, respectively, preferably have between 4 and 30 each, more preferred between 6 and 20, yet more preferred between 8 and 18 carbon atoms. Phospholipids comprising two alkanoic acids may either symmetric or asymmetric. In the latter case, a phospholipid molecule comprises two different fatty acids. In another preferred embodiment, the phospholipds are of natural origin, like for example phosphatidylinositol.

On the other hand, preferred counter ions for acidic polymers (for example heparin) or other acidic pharmaceutically or diagnostically active agents are phospholipids that carry a positive charge. Preferably they have a free primary amino group like, but not limited to phosphatidyl serine and phosphatidyl ethanolamine.

An increased lipophilicity of the counter ion increases the stability of the complex between a cyclic compound such as a cyclic polyester, polyorthoester, polyamide or depsipeptide of the invention with said primary and/or secondary protonated amino group and/or protonated guanidinium group.

In a further preferred embodiment of the uses and methods of the invention, the ring comprised in said compound consists of between 9 and 90 atoms, wherein said ring comprises all occurrences of X and Y. When used to designate a feature of the compound of the invention as a whole, the term "ring" refers to a ring which includes all functional groups X and Y as opposed to cycle which may be present within one or more of the monomers. When the number of atoms in said ring is to be determined, any substituents or exocyclic atoms are disregarded. For example, both cyclic poly-glycolic acid and cyclic poly-lactic acid comprise a ring of the following structure; (—O—C—C(=O)—)$_n$; n being an integer number, the central C atom being optionally substituted, and oxygen of the carbonyl group not being part of the ring as defined above. Staying with these examples, a 9-membered ring of an alpha hydroxyl acid specifies a trimeric cyclic polyester, and a 48-membered ring specifies a 16-meric cyclic polyester.

Preferably, the ring comprised in said cyclic polyester, polyorthoester, polyamide or depsipeptide consists of 18 to 48 atoms, more preferred of 18 to 36 and yet more preferred of 18 to 24 atoms.

It is furthermore preferred that the monomers of said cyclic polyester or polyorthoester or the hydroxy acid monomers, if present, of said cyclic compound belonging to more than one of (i) to (vii) include or are exclusively alpha-hydroxy acids.

Analogously it is preferred that the monomers of said cyclic polyamide or the amino acid monomers, if present, of said cyclic compound belonging to more than one of (i) to (vii) include or are exclusively alpha-amino acids.

More preferred, said cyclic compound belonging to more than one of (i) to (vii) is a depsipeptide and the alpha-hydroxy acids and alpha-amino acids alternate in said depsipeptide.

Preferred alpha-hydroxy acids are glycolic acid and lactic acid.

A preferred alpha-amino acid is glycine.

A preferred cyclic polyamide is esaglycine.

In a further preferred embodiment of the uses and methods of the invention, one or more of said alpha-hydroxy acids is glycolic acid and/or one or more of said alpha-amino acids is glycine, the alpha carbon atom of one or more of said glycolic acids and/or glycines being substituted with a linear or branched alkyl group with 1, 2, 3, 4, 5, 6, 7, 8, 9 or 10 carbon atoms or with a substituted or unsubstituted aryl group. Suitable alkyl substituents include methyl, ethyl, n-propyl, i-propyl, n-butyl, i-butyl, t-butyl, n-pentyl, i-pentyl, 2-methyl butyl, n-hexyl, i-hexyl, 2-methyl pentyl, 3-methyl pentyl and 2-ethyl butyl. In a further preferred embodiment, said linear or branched alkyl group may carry a terminal hydroxy group. This hydroxy group (which is a second hydroxy group in case of an alpha-hydroxy acid) permits further derivatization, for example, by esterification with alkanoic acids or the like. A preferred aryl group is phenyl. The same applies mutatis mutandis to alpha aminoxy acids. A preferred alpha aminoxy acid is aminoxy glycin, which optionally may be substituted as described above.

Preferably, monomers with an alkyl group with N carbon atoms or an aryl group and monomers with an alkyl group with N+K carbon atoms alternate in said compound, wherein N is selected from 0 and 1 and K is selected from 1, 2, 3, 4, 5, 6, 7, 8, 9 and 10. The term "alternate" implies an even number of monomers. Preferred compounds such as cyclic polyesters, polyorthoesters, polyamides or depsipeptides are 4-mers, 6-mers, 8-mers, 10-mers, 12-mers, 14-mers and 16-mers.

Preferably, said cyclic polyester or polyorthoester is cyclic polylactic, polyglycolic or poly(lactic, glycolic) ester or orthoester.

More preferred, lactic acid monomers and glycolic acid monomers alternate in said cyclic polyester or cyclic polyorthoester.

In a preferred embodiment of the uses and methods of the invention, said cyclic polyester or polyorthoester is nonactin (see FIG. 2) or a cyclic tetra-, penta-, hexa-, hepta-, octa-, nona- or decamer of lactic acid, of glycolic acid, or of lactic and glycolic acid. As regards tetra-, hexa- and octamers of lactic and glycolic acid, it is preferred that lactic acid monomers and glycolic acid monomers alternate. The term "alternate" as used herein refers to sequences of monomers x, y such as xyxyxy. However, also other sequences such as xxyyxxyy or irregular sequences are envisaged.

A further preferred cyclic polyester or cyclic polyorthoester is a cyclic tetra-, hexa-, octa- or decamer of a chiral alpha-hydroxy acid such as lactic acid, wherein R-form and S-form monomers alternate. As stated above, cyclic polyorthoesters are valence tautomers of cyclic polyesters.

Alternating sequence of R- and S-forms of other chiral acids are also envisaged. Examples include mandelic acid as well as chiral naturally occurring amino acids, wherein the naturally occurring L-form would alternate with the D-form.

In a preferred embodiment of the uses and methods of the invention, said active agent is a (a) peptide, polypeptide, protein or antibody; (b) a salt comprising a primary or secondary amine; or (c) a salt comprising a compound comprising a guanidinium group. The terms "peptide", "polypeptide" and "protein" include compounds which comprise one or more non-naturally occurring amino acids such as beta-alanine, alpha-amino butyric acid, gamma-amino butyric acid, alpha-amino isobutyric acid, norvaline, norleucine, epsilon-lysine, ornithine, homoserine and hydroxyproline. Furthermore, reactive groups including N- and C-terminus may be blocked by protection groups. Also further derivatizations of peptides, polypeptides and proteins known in the art, including naturally occurring post-translational modifications, are deliberately included.

Examples of pharmaceutically active agents which are salts comprising a primary or secondary amine are ibuprofen lysinate, i.e. the lysine salt of ibuprofen and procaine penicillin. In case of ibuprofen lysinate, ibuprofen is the component of said salt providing a carboxylate and lysine is the component providing a primary amino group. Similary, in case of procaine penicillin, penicillin is the component of said salt providing a carboxylate and procaine is the component providing a primary and a secondary amino group. While these are just specific examples, it is envisaged that any drug which (i) comprises a carboxylic acid functional group and (ii) is a salt with a compound comprising a primary or secondary amine or a guanidinium group may be formulated as a complex with a compound of the invention. Such drugs include anti-inflammatory drugs fulfilling these two requirements including ibuprofen lysinate as well as antibiotics such as procaine penicillin or aminoglycosides. FIG. 4(B) illustrates this principle.

Preferably, said active agent being a peptide, polypeptide or protein comprises one or more amino acids selected from Lys, Arg, His and Trp. Lys and Arg are most preferred.

In a preferred embodiment of the uses and methods of the invention, said active agent being a peptide, polypeptide or protein comprises one or more amino acids selected from Asp and Glu.

Preferably, said pharmaceutical or diagnostic composition is acidic. This embodiment is directed to active agents which in addition to protonated primary and/or protonated secondary amino groups and/or a protonated guanidinium groups comprise groups which are negatively charged at neutral pH such as the carboxylates of Asp and Glu in peptides, polypeptides and proteins. In such a case, the aim of forming a complex with compounds of the invention, which is increasing hydrophobicity and shielding of charges might not be achieved as regards said groups which are negatively charged at neutral pH such as the carboxylates of Asp and Glu. One option of removing the charges to acidify the composition to a pH where a significant fraction of said groups which are negatively charged at neutral pH become protonated and in consequence uncharged.

More preferred, said pharmaceutical or diagnostic composition has a pH-value between 2 and 6. Yet more preferred, the pH-value is between about 4 and about 5.

Figure 3:
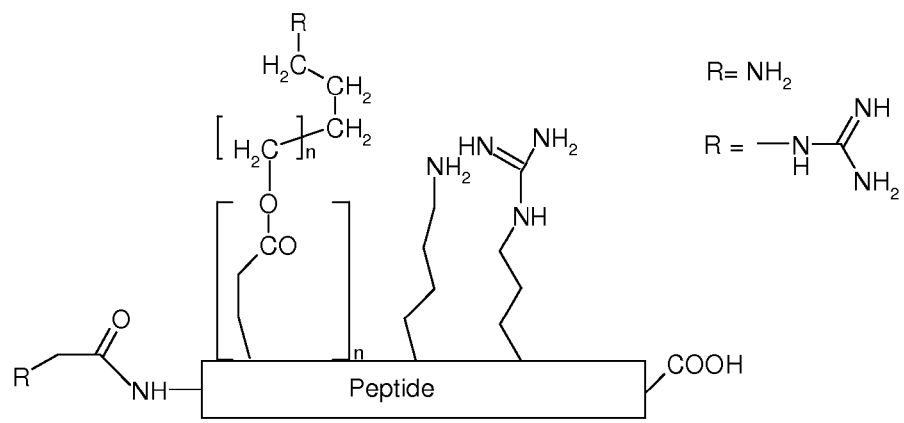

Alternative to said pharmaceutical or diagnostic composition being acidic or in addition thereto, one or more of the Asp or Glu residues are esterified with an amino alcohol and/or guanidinium alcohol, wherein the amino group of said amino alcohol is a primary or secondary amino group. An illustration of the esterification of Asp and/or Glu residues is shown in FIG. 3. Preferably, the majority (i.e. more than 50%), more preferred 60%, 70%, 80%, 90%, 95%, 98%, 99% or all of said Asp or Glu residues are esterified. The esterification leads to the formation of a prodrug. A "prodrug" is a compound that is generally not biologically and/or pharmacologically active. However, when activated, typically in vivo by enzymatic or hydrolytic cleavage to convert the prodrug to a biologically and/or pharmacologically compound, the administration of the prodrug will have the intended medical effect. Prodrugs are typically formed by chemical modification such as by the above described esterification of biologically and/or pharmacologically compounds. Conventional procedures for the selection and preparation of suitable prodrug derivatives are described, for example, in Design of Prodrugs, ed. H. Bundgaard, Elsevier, 1985.

Preferably, said amino alcohol is an omega-amino-alkyl-ol.

Preferably, said amino alcohol is 4-amino-1-butanol or 6-amino-1-hexanol. The esterified form of Asp and/or Glu is herein referred to as "pseudo-lysine", since a structure is generated which is similar to Lys in that a linear alkyl chain is bound with one of its termini to the carboxylate (via an ester bond), wherein the alkyl chain carries a primary amino group at the other terminus. Alternatively or in addition, omega-guanidinium-alcohols may used, thereby generating "pseudo.arginines".

In a preferred embodiment, (i) an excess of said compound is used; and/or (ii) a second compound according to the invention is used, wherein said second compound preferably forms a complex with a cation, said cation being a counter ion of the carboxylate of said Asp and/or Glu. The term "cation" includes inorganic cations. Inorganic cations include metal ions such as $Na^+$ and $K^+$. Alternative or addition to the options of acidifying the composition, esterifying said Asp and/or Glu, this embodiment provides two further options. Any of these four options may be used alone or in combination.

The term "excess" relates to amounts of said compound which exceeds an equimolar amount of said primary and/or secondary amino groups and/or guanidinium groups to be complexed. Such excess may be used to ensure complexation of a substantial fraction or all of said primary and/or secondary amino groups and/or guanidinium groups to be complexed. While equimolar amounts may be sufficient to this end, it is preferred to use an excess such as a three- to ten-fold molar excess or more preferably three- to five-fold molar excess.

Any excess amount not involved in complexes with primary and/or secondary amino groups and/or guanidinium groups will be available for the complexation of cations which serve as counter ions of the negatively charged carboxylates present on said Asp and/or Glu residues. To ensure complexation of these counter ions as well (in addition to complexation of a substantial fraction or all of said primary and/or secondary amino groups and/or guanidinium groups), a preferred amount of cyclic compound such as cyclic polyester, polyorthoester, polyamide, depsipeptide, polyether and/or polyoxime is a five- to seven-fold molar excess of the amount of carboxylates. As a consequence, it is preferred to use an amount of said compound which is a sum of a three- to five-fold molar excess of the amount of primary and/or secondary amino groups and/or guanidinium groups and a five- to seven-fold molar excess of the amount of carboxylates. Such complexation of cations by cyclic compounds of the invention designed to complex primary and/or secondary amino groups and/or guanidinium groups will work the better the less specific the complexation of said primary and/or secondary amino groups and/or guanidinium groups is. In case cyclic compounds of the invention are used which complex said primary and/or secondary amino groups and/or guanidinium groups with a high degree of specificity, it is preferred to use a second cyclic compound of the invention such as a cyclic polyester, polyorthoester, polyamide and/or depsipeptide, wherein said second cyclic compound preferably forms a complex with said cation, said cation being for example a metal ion. In those cases said compound which complex said primary and/or secondary amino groups and/or guanidinium groups are referred to as "first" compounds. In a further preferred embodiment, the first cyclic compound and/or the second cyclic compound are capable of forming a complex with an ammonium ion ($NH_4^+$).

The term "metal ion" as used herein refers to any metal ion. Preferably it relates to ions of those metals which are present in the human body. Specific preferred metal ions include $Na^+$, $K^+$, $Ca^{2+}$ and $Mg^{2+}$.

Preferably, said active agent is a small organic molecule. The compositions of the invention may comprise a small organic molecule as the only active agent. Alternatively, they may comprise a plurality of active agents, wherein said active agents preferably are selected from the group consisting of peptides, polypeptides, proteins and small organic molecules. Small organic molecules preferably have a molecular weight of about 500 Da or below. However, also active agents which not necessarily are peptides, polypeptides, proteins and having a molecular weight between 500 and 5000 Da are envisaged.

The present invention also provides the use of a cyclic compound of formula (I)

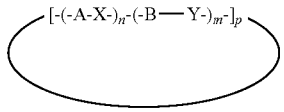

wherein A, B independently in each occurrence is alkane-i,j-diyl having k carbon atoms, i and independently j being less than or equal k and k being selected from 1 to 10, wherein said alkane-i,j-diyl (i) may comprise one or more double bonds; (ii) is optionally substituted; and/or (iii) comprises a cycle, wherein the total number of cycles being cyclic sugars in said compound is selected from 0 to 4 and is less than p·(n+m); X,Y independently in each occurrence is a biocompatible functional group comprising at least one oxygen atom or two sulphur atoms; n, m independently of each other are selected from 0 to 20; p is selected from 1 to 10; n+m is equal or greater than 1; and p·(n+m) is selected from 3 to 30; wherein said compound is capable of forming a complex with a metal ion, for the manufacture of a pharmaceutical or diagnostic composition further comprising a pharmaceutically or diagnostically active agent, said active agent forming a salt with said metal ion, wherein (a) transmembrane and/or transmucosal delivery; (b) solubility in non-aqueous solvents; and/or (c) stability of said active agent are improved. Preferred pharmaceutically or diagnostically active agents are peptides, polypeptides, proteins, antibodies and small organic molecules. Assays for the assessment of the capability to form a complex are known in the art and described herein above. These assays are applied mutatis mutandis to the determination of cyclic compounds which are capable of forming a complex with a metal ion. Active agents forming a complex with said metal include active agents comprising a negative charge such as a negatively charged carboxylate. An example is illustrated in FIG. 4(A).

It is understood that all preferred embodiments of the main embodiment, to the extent said preferred embodiments provide a further structural characterization of the compound of the invention, apply mutatis mutandis to the use according to the invention disclosed right above.

In addition to pharmaceutically or diagnostically active agents, constituents of functional food or food supplements may be complexed with the above mentioned cyclic polyesters, polyorthoesters, polyamides and depsipeptides of the invention, provided that the constituent of a functional food or the constituent of a food supplement forms a salt with one or more metal ions. Such constituent (also referred to as active agent) may take the place of the pharmaceutically or diagnostically active agents in the uses and methods of the invention.

Accordingly, the present invention also relates to use of a cyclic compound of the invention; wherein said cyclic compound is capable of forming a complex with a metal ion for improving (a) transmembrane and/or transmucosal delivery; (b) solubility in non-aqueous solvents; and/or (c) stability of an active agent, wherein said active agent forms a salt with one or more metal ions. The term active agent comprises pharmaceutically active agents or drugs, diagnostically active agents as well as constituents of functional food and constituents of food supplements.

The term "pharmaceutically or diagnostically active agent" as used herein also includes complex polysaccharides such as heparin. Heparin is a heterogeneous group of straightchain anionic mucopolysaccharides, called glycosaminoglycans having anticoagulant properties. Although others may be present, the main sugars occurring in heparin are: (1) α-L-iduronic acid 2-sulfate, (2) 2-deoxy-2-sulfamino-α-D-glucose 6-sulfate, (3) β-D-glucuronic acid, (4) 2-acetamido-2-deoxy-α-D-glucose, and (5) α-L-iduronic acid. These sugars are present in decreasing amounts, usually in the order (2)>(1)>(4)>(3)>(5), and are joined by glycosidic linkages, forming polymers of varying sizes. Heparin is strongly acidic because of its content of covalently linked sulfate and carboxylic acid groups. In heparin sodium, the acidic protons of the sulfate units are partially replaced by sodium ions. Shown below is a representative fragment of heparin Sodium:

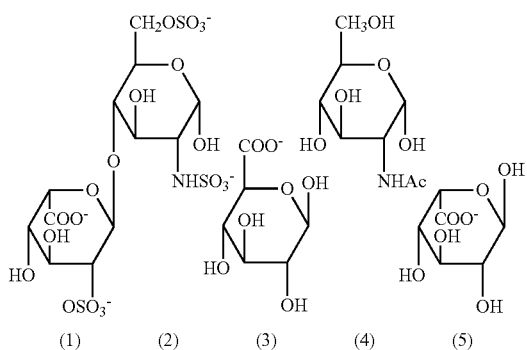

Heparin Sodium, and Heparin Calcium have been approved as medicaments. The uses of the present invention is expected to permit an enhancement of absorption, delivery and/or stability (half life) of Heparin Sodium and Heparin Calcium. The same is expected to apply to a lysine salt of heparin.

Preferably, said compound is biodegradable.

Preferably, said compound is capable of selectively forming a complex with said metal ion.

Preferred compounds capable of forming a complex with a metal ion which are polyesters are selected from nonactin (see FIG. 2) and tetranactin. Preferred compounds capable of forming a complex with a metal ion which are depsipeptides are selected from valinomycin and enniatin B.

Preferably, said pharmaceutical or diagnostic composition is to be delivered in a non-invasive way such as orally, buccally, sublingually, nasally, pulmonary, dermally, transdermally, ocularly and/or rectally. The term "buccally" includes compositions which are absorbed in the mouth. As stated above, it is one of the advantages of the present invention that active agents which so far could only be delivered in an invasive manner can no be obtained in their complexed form with cyclic polyesters, polyorthoesters, polyamides or depsipeptides of the invention and administered in a non-invasive manner. Also preferred for the reasons stated above is subcutaneous administration.

The present invention also relates to a method of preparing a pharmaceutical or diagnostic composition with improved transmembrane and/or transmucosal delivery and/or improved stability, comprising the step of (a) bringing into contact a pharmaceutically or diagnostically active agent comprising one or more primary and/or secondary protonated amino groups and/or protonated guanidinium groups with a compound of the invention, wherein said compound is capable of forming a complex with a primary or secondary protonated amino group or a protonated guanidinium group.

Said bringing into contact is to be effected under conditions suitable for formation of a complex between the one or more primary and/or secondary protonated amino groups and/or protonated guanidinium groups with said compound.

Conditions suitable for complex formation include a solution of said pharmaceutically or diagnostically active agent and of said compound in an organic solvent. Preferred organic solvents are polar and/or protic solvents such as methanol or ethanol. Alternatively, also apolar and aprotic solvents such as dichloromethane may be used. In a preferred embodiment of the method of the invention, said bringing into contact occurs in a solution of said pharmaceutically or diagnostically active agent and of said compound in a polar and/or protic solvent. In a further preferred embodiment, said polar and/or protic solvent is subsequently removed, for example by evaporation. In a more preferred embodiment, the complex obtained upon evaporation is taken up in an apolar and aprotic solvent. This two-step procedure of preparing a complex dissolved in an apolar and aprotic solvent may yield solutions of said active agent of higher concentration as compared to the "direct" procedure of combining active agent; cyclic polyester, polyorthoester, polyamide and/or depsipeptide and apolar and aprotic solvent.

The preferred embodiments of uses of the invention translate mutatis mutandis to preferred embodiments of the methods of the invention.

Preferably, an excess of said compound is used.

In a further preferred embodiment of the method of the invention, said active agent is a peptide, polypeptide or protein comprising one or more amino acids selected from Asp and Glu and the method comprises the further step(s) of (b) acidifying said pharmaceutical or diagnostic composition; (c) esterifying one or more of the Asp or Glu residues with an amino alcohol, wherein the amino group of said amino alcohol is a primary amino group; and/or (d) bringing into contact with said pharmaceutically or diagnostically active agent one or more further compounds of the invention, wherein said further compound(s) preferably form(s) a complex with a metal ion, said metal ion being a counter ion of the carboxylate of said Asp and/or Glu.

The present invention also relates to a method of preparing a pharmaceutical or diagnostic composition with improved transmembrane and/or transmucosal delivery and/or improved stability, comprising the step of bringing into contact a pharmaceutically or diagnostically active agent, wherein said active agent is a salt with a metal ion, with a compound of the invention, wherein said compound of the invention is capable of forming a complex with said metal ion.

Preferably, a non-aqueous solvent is added to said pharmaceutical or diagnostic composition.

Furthermore, the present invention provides compounds suitable for practising the claimed uses and methods.

Accordingly, the present invention provides a compound selected from (a) a cyclic tetrameric, hexameric or octameric polyester or polyorthoester, wherein glycolic acid monomers substituted in alpha position with a linear or branched alkyl group with N carbon atoms and glycolic acid monomers substituted in alpha position with a linear or branched alkyl group with N+K carbon atoms alternate, wherein N is selected from 0 and 1 and K is selected from 1, 2, 3, 4 or 5; (b) a cyclic hexamer, heptamer or octamer of glycolic acid, or of lactic and glycolic acid; (c) a cyclic heptamer of lactic acid; and (d) a cyclic tetrameric, hexameric or octameric depsipeptide, wherein alpha-hydroxy acids having between 2 and 10, preferably between 2 and 6, more preferred between 2 and 4 carbon atoms, and glycine alternate in said depsipeptide Preferably, the monomer with an alkyl group with N carbon atoms is glycolic acid and the monomer with an alkyl group with N+K carbon atoms is lactic acid.

Preferably, the alpha-hydroxy acid is glycolic or lactic acid.

The present also provides a pharmaceutical or diagnostic composition comprising one or more compounds according to the invention.

The Figures show:

FIG. 1: Schematic drawing illustrating transmucosal delivery of a (poly)peptide complexed with a poly-lactic acid hexamer.

FIG. 2: Examples of polyesters and polyamides of the invention.

FIG. 3: Schematic drawing of the esterification of carboxylates of Asp and Glu on peptides.

Figure 4:
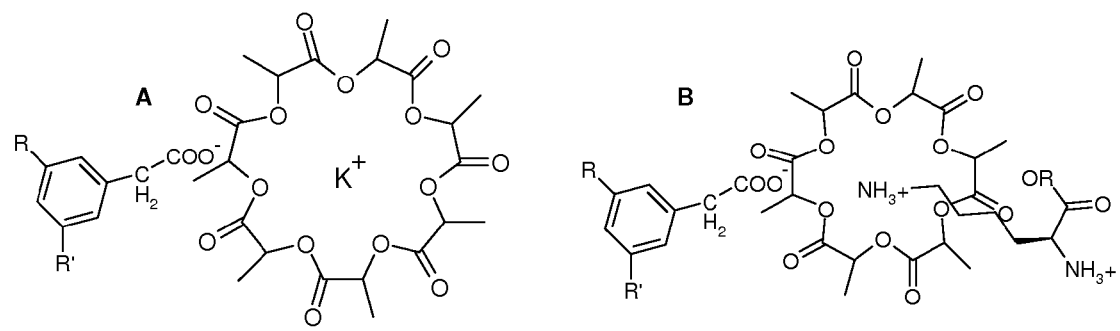

FIG. 4: Complexation of small molecules with a cyclic polyester. (A) Potassium salt of a small molecule, wherein the potassium ion forms a complex with a cyclic polyester. (B) Lysine salt of a small molecule, wherein the protonated primary amino group of lysine forms a complex with a cyclic polyester.

Figure 5:
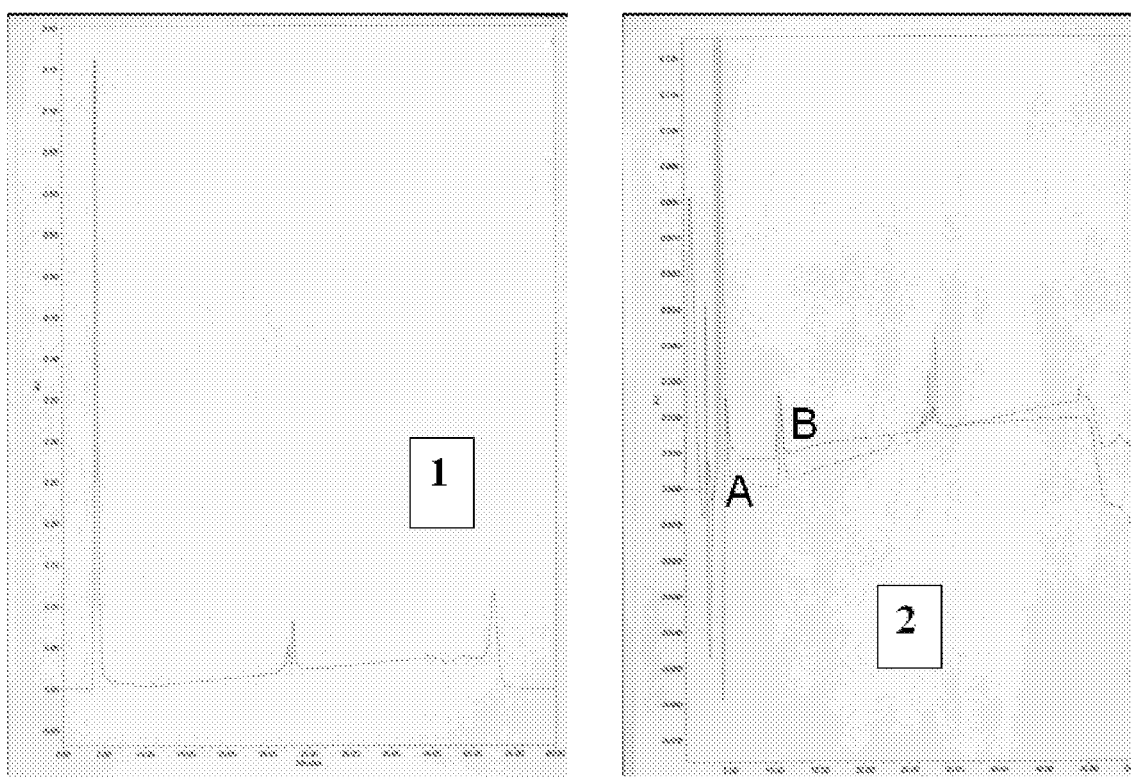

FIG. 5: left panel: M8 dissolved in water and acetonitrile (Standard). The HPLC shows two peaks due to original methionine oxidation. Right panel: M8 complex with cyclic esaglycine: (A) Methanol solution after removal of (solid) centrifuged material; (B) material after centrifugation re-dissolved in water acetonitrile. Both in experiments A and B an equal volume of solution has been injected.

Figure 6:
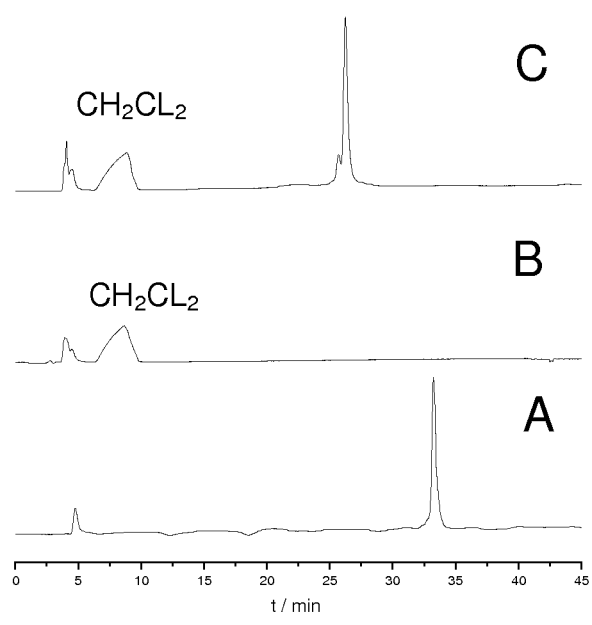

FIG. 6: HPLC traces of the chemokine RANTES complexed with Nonactine.

Figure 7:
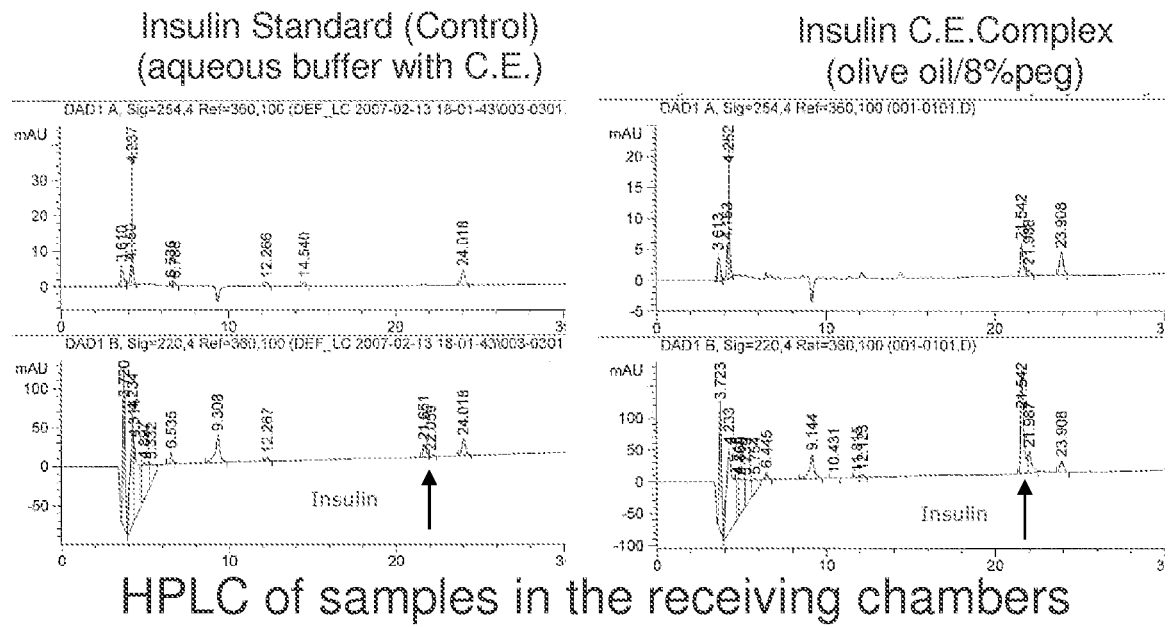

FIG. 7: Insulin delivery through Caco-2 cells. HPLC traces of Insulin in the receiving chambers. The receiving chamber collects the solution coming through Caco-2 cells.

Figure 8:
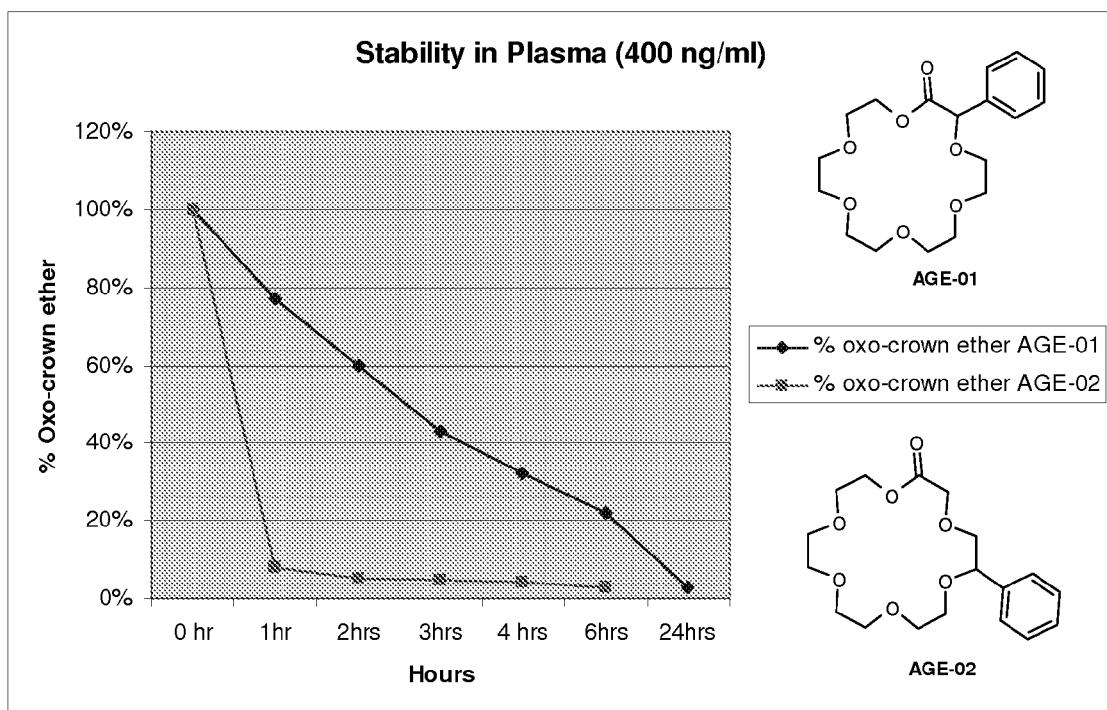

FIG. 8: Stability test of oxo-crown ethers in plasma

Figure 9:
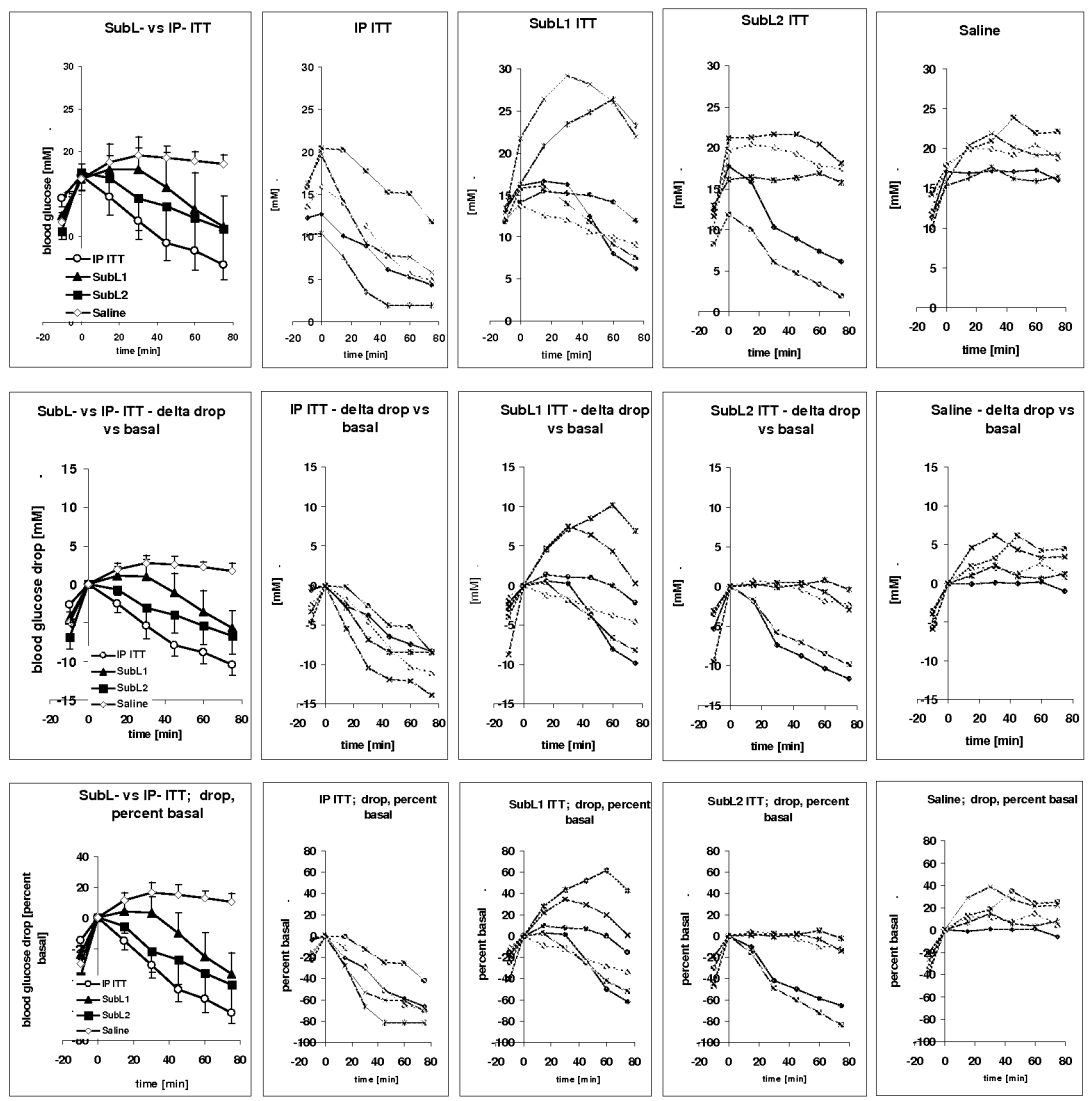

FIG. 9: Blood glucose level measurements upon insulin sub-lingual delivery in mice. PI ITT=effects of standard Insulin obtained by injection. SubL1 ITT: Dose 1 via sublingual administration. SubL2 ITT: Dose 2 via sublingual administration.

Figure 10:
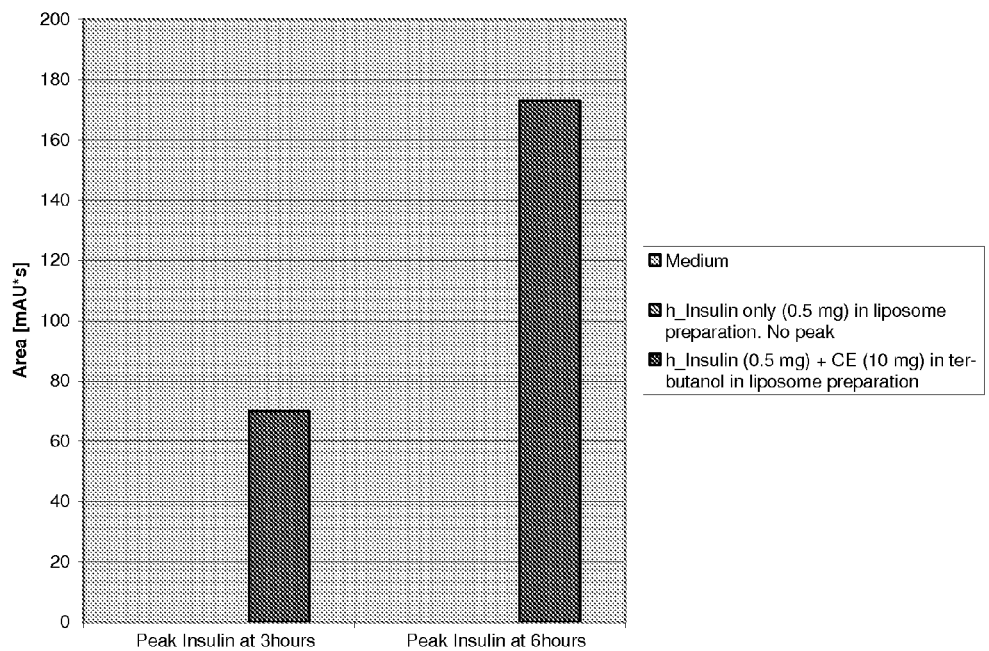
Figure 10:
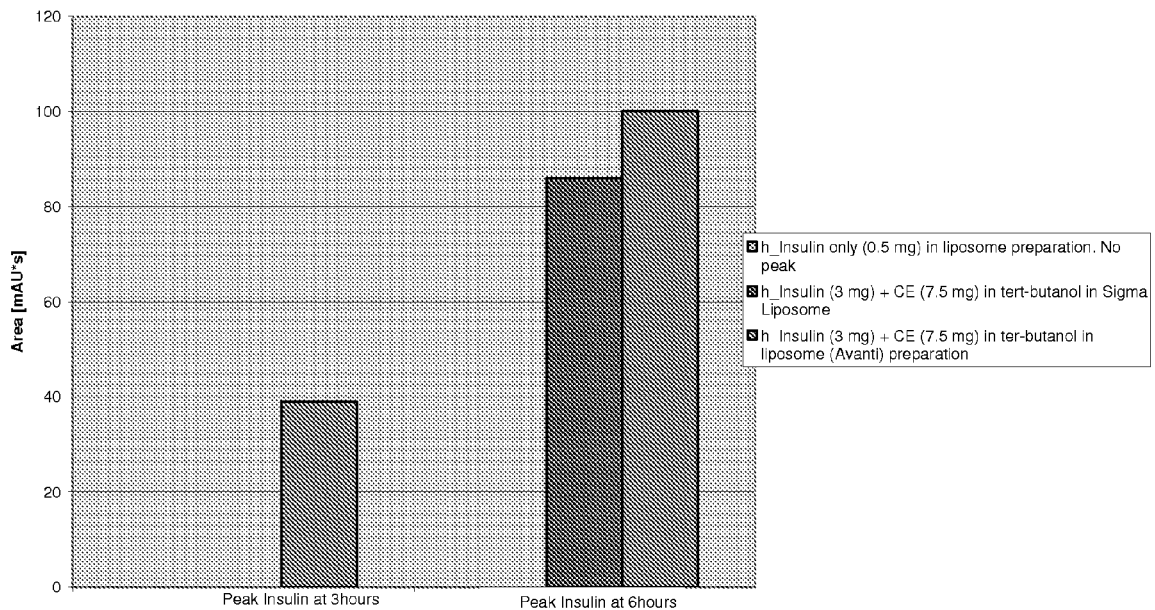

FIG. 10: Insulin delivery in Liposomes through Caco-2 cells.

The following examples illustrate the invention but should not be construed as being limiting.

EXAMPLE 1

Preparation and use of Cyclic Esaglycine Polymer

Cyclic esaglycine polymer was prepared according to Cardona et al. *Journal of Peptide Research,* 2003, 61, 152-157.

After Reverse Phase chromatography purification, the cyclic esaglycine was use to complex and dissolve into organic solvent such as methanol a model chemokine called M8 having the sequence as follows: MSPPLMQTTPCCFAY-IARPLPRAHIKEYFYTSGKCSNPAV-VFVTRKNRQVCANPEK KWVREYINSLEMS (SEQ. ID NO:1). The solution of the esaglycine-protein complex in methanol was centrifuged to determine the amount of protein not dissolved in the organic solvent. After centrifugation, the organic solution was transferred in a second vial and the original vial was washed with water/acetonitrile to re-dissolve the protein eventually precipitated. The HPLC chromatograms of FIG. 5 show a) the methanol solution after complexation and centrifugation, and b) the water/acetonitrile solution used to wash the centrifugation vial.

EXAMPLE 2

Synthesis and Characterization of Oxo-Croxn Ester Cyclic Compounds

This example describes the preparation of various oxo-crown ethers (Scheme 1). Synthesis of AGE-01 is described in Matsushima et al. Bull. Chem. Soc. Jpn., 1982, 55, 2181-2185. However the synthesis of AGE-02 as well as AGE-04 were never performed before. Synthesis in analogy to synthesis of oxo-crown ethers as described in Meijer et al. Macromolecules, 1997, 30, 8113-8128 was considered to be the most promising approach.

Scheme 1: overview on the oxo-crown ethers

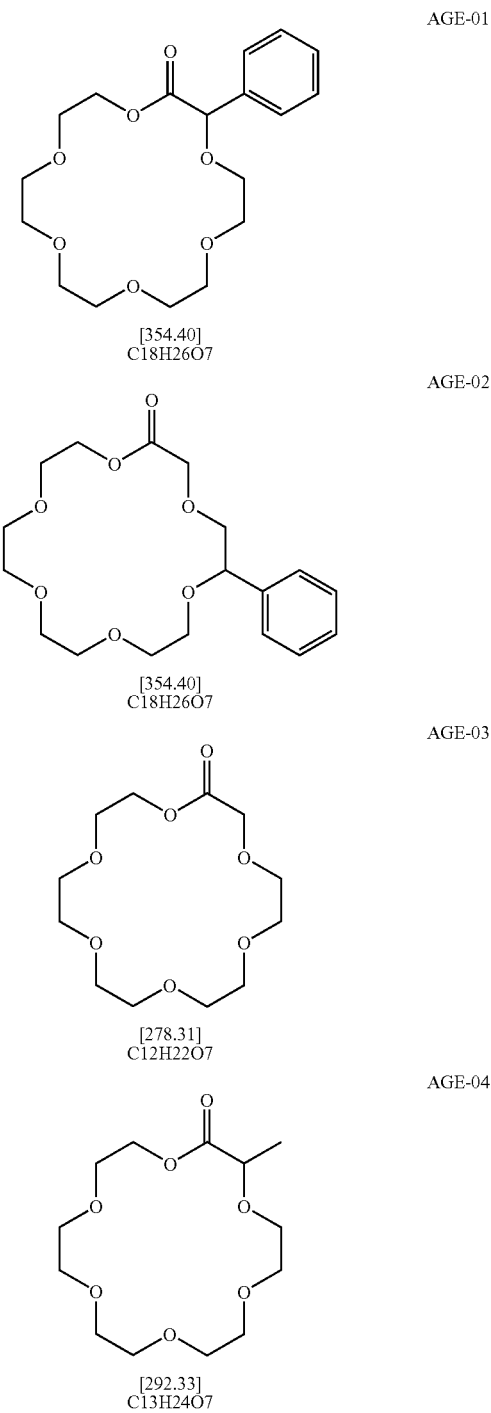

The synthetic pathway leading to AGE-01 is summarized on scheme 2; the approach differs completely from the route described in the literature. Indeed, pyrolysis conditions needed for the cyclisation step are not applicable for scale up, therefore an alternative approach had to be elaborated.

The target molecule AGE-01 is obtained in a 5-steps synthesis.

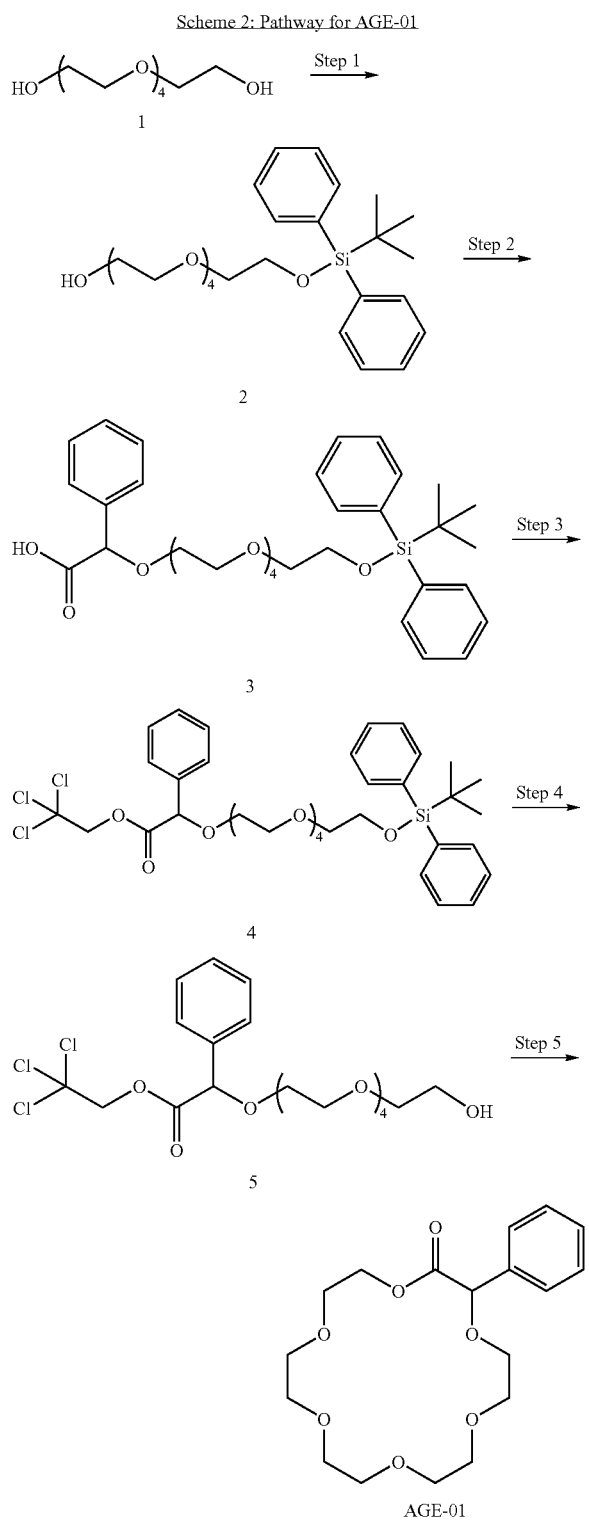

As shown in scheme 2 the synthesis starts with the selective monoprotection of the pentaethylene glycol. Pentaethylene glycol 1 was reacted with tert-butyldiphenylsillyl chloride in the presence of sodium hydride to give the monoprotected derivative 2 with 75% of yield after chromatography purification. Only a small amount of diprotected diol was observed. In step 2, alpha-bromophenylacetic acid was treated with a large excess of NaH in THF followed by the drop wise addition of a solution of monoprotected diol 2 in DMF. After standard work up, the carboxylic acid 3 was isolated in high yield (86%-quantitative yield). The acid 3 was used in next step without further purification. Synthesis of ester 4 was carried out from the carboxylic acid 3 by reaction with the trichloroethanol, DCC and DMAP in dry THF. The trichloroethylester 4 was isolated as colorless oil in moderate to good yield (70%).

Although the silyl deprotection was performed using TBAF (5 eq.) in THF, a large amount of decomposition was observed. The low stability of the trichloroethylester 4 required to change the initial conditions. In order to avoid decomposition, the reaction was performed in presence of a large excess (87 eq.) of glacial acetic acid. In this case, full deprotection was observed by overnight reaction and 4 was isolated after purification by chromatography on silica gel with 60% of yield. The use of a reduce amount of acetic acid (5 eq.) allowed to accelerate the reaction and only few minutes were needed for clean full deprotection.

Attempt of direct cyclisation of the trichloroethylester 4 in presence of a large excess (10 eq.) of base such as $K_2CO_3$ in diluted conditions afforded the oxo-crown ether AGE-01 in moderate yield (64%).

During the silyl deprotection of 4 using the TBAF/AcOH conditions already trace of AGE-01 was observed. One pot reaction could be envisaged and after deprotection of the sillyl moiety, the reaction mixture was diluted with THF and treated over night with $K_2CO_3$ (15 eq.). AGE-01 was isolated in good yield (74%) over two steps.

1H-NMR and MS are in accordance with the structure. Simple reactions to discard the seco acid rather than the oxo-crown ether were attempted. Hydrolysis of the trichloroethylester 5 under reductive condition using Zn dust in 90% AcOH/water as well as under basic conditions (LiOH/THF/MeOH) afforded the corresponding seco acid.

Ring opening of the oxo-crown AGE-01 using LiOH gave as well the corresponding seco acid.

AGE-01:

$^1$H-RMN (500 MHz, CDCl$_3$): 3.62-3.78 (m, 20H); 4.04-4-10 (ddd, J=2.6, 5.6, 9.1, 1H), 4.41-4.47 (ddd, J=2.6, 7.2, 9.7, 1H), 7.31-7.40 (m, 3H), 7.46-7.52 (m, 2H); MS m/z calcd. for [M+H]$^+$: 355, found 355, 377(+Na) and 393 (+K).

The second oxo-crown ether AGE-02 differs of AGE-01 by the position of the phenyl moiety (Scheme 3).

Scheme 3: sythensis of AGE-02
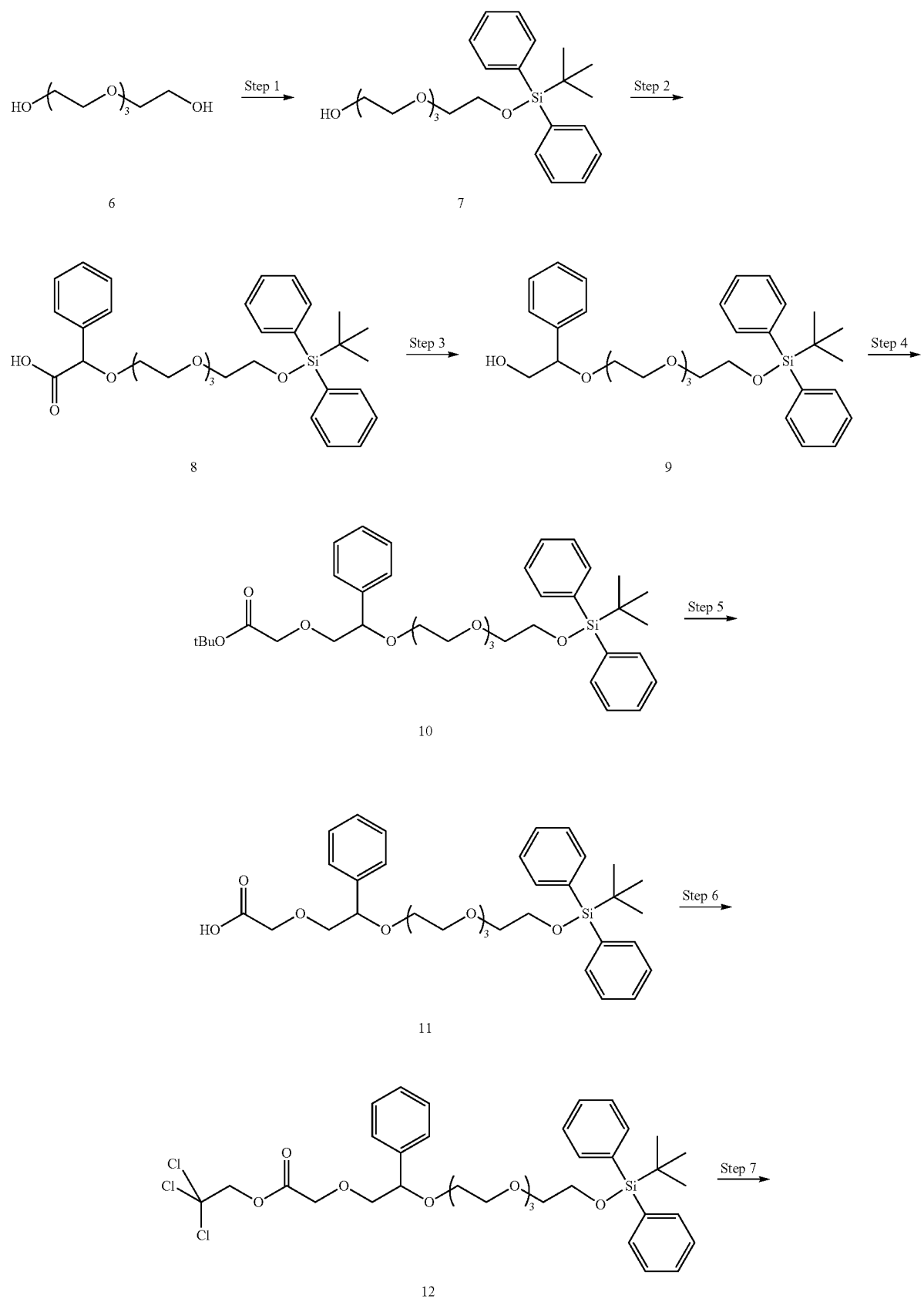

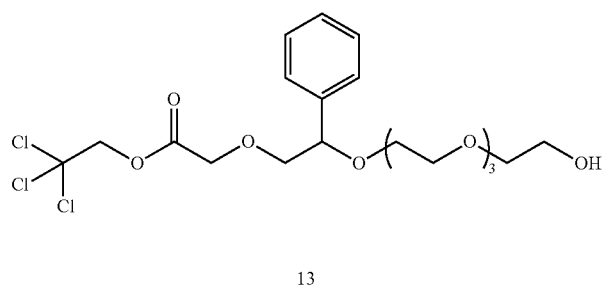

13

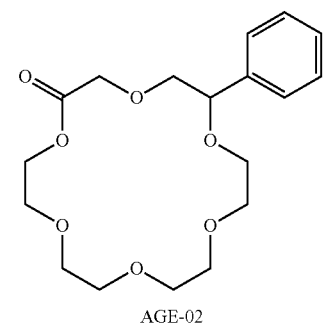

AGE-02

As shown in scheme 3 the synthesis starts with the selective monoprotection of the tetra ethylene glycol. Tetra ethylene glycol 6 was reacted with tert-butyldiphenylsillyl chloride in the presence of sodium hydride to give the monoprotected derivative 7 in moderate yield (63%) after chromatography purification. In this case, more deprotected diol was observed than for the protection of pentaethylene glycol. In step 2, alpha-bromophenylacetic acid was treated with a large excess of NaH in THF followed by the drop wise addition of a solution of monoprotected diol 7 in DMF. After standard work up, the carboxylic acid 8 was isolated in quantitative yield. The acid 8 was used in next step without further purification.

The carbonyl moiety of 8 was reduced with the complex $BH_3$.THF in THF at 0° C. then room temperature to give the alcohol 9 in low to high yield. Purification of the alcohol 9 by chromatography on silica gel afforded 9 only in low yield (31%). Therefore, the alcohol 9 was not purified by chromatography on silica gel and was used directly in next step after standard work up.

Coupling reaction with tert-butylbromoacetate and t-BuOK in t-BuOH gave the corresponding ester 10 without major problems with 50% of yield after purification on silica gel. Deprotection of the tert-butyl ester moiety was performed first using aqueous LiOH in THF/MeOH to give the carboxylic acid 11 in quantitative yield. The crude material was directly used in next step without further purification. Synthesis of ester 12 was carried out by reaction of 11 with trichloroethanol, DCC and DMAP in dry THF. The ester 12 was isolated as colorless oil in moderate yield (55%) after chromatography purification. Sillyl deprotection was performed without major problem using 5 eq. of TBAF in THF and AcOH (5 eq.). After work up and purification, 13 was isolated in 73% yield. Attempt of cyclisation of the trichloroethylester 13 in presence of a large excess (10 eq.) of base such as $K_2CO_3$ in diluted conditions afforded the Oxo-crown ether AGE-02 with 47% of yield as slightly yellow oil which slowly solidified. Direct cyclisation from 12 with 15 eq. $K_2CO_3$ after TBAF treatment without work up and isolation of the intermediate gave better yield of AGE-02 (89% for 2 steps).

AGE-02:

MS m/z calcd. for $[M+H]^+$: 355, found 355, 377(+Na) and 393 (+K)

The synthetic pathway leading to AGE-05 is summarized on scheme 4; the strategy used for AGE-01 was applied. Indeed, the coupling reaction on step 2 is performed using the 2-bromopropionic acid rather than alpha-bromophenylacetic acid.

The target molecule AGE-04 is obtained in a 5-steps synthesis.

Scheme 4: synthesis of AGE-05

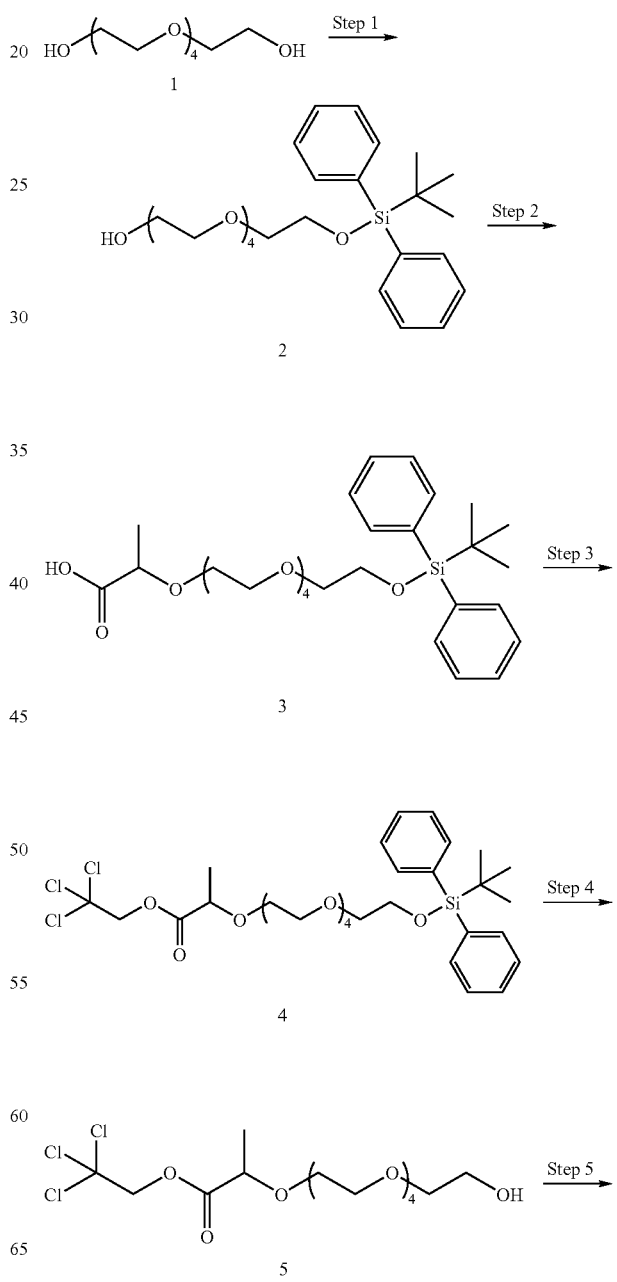

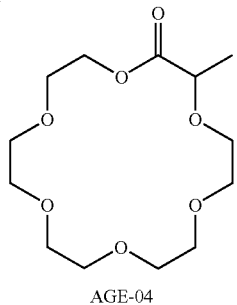

AGE-04

As shown in scheme 4 the synthesis starts with the selective monoprotection of the pentaethylene glycol. On step 2, 2-bromopropionic acid was treated with a large excess of NaH in THF followed by the drop wise addition of a solution of monoprotected diol 2 in DMF. After standard work up, the carboxylic acid 3 was isolated in high yield (quantitative yield). The acid 3 was used in next step without further purification. Synthesis of ester 4 was carried out from the carboxylic acid 3 by reaction with the trichloroethanol, DCC and DMAP in dry THF. The trichloroethylester 4 was isolated as colorless oil in moderate yield (56%).

Although the silyl deprotection performed using TBAF (5 eq.) and AcOH (5eq.) in THF, the product was not isolated and the reaction mixture was directly treated with a large excess of $K_2CO_3$ after dilution with THF. Under these condition, the oxo-crown AGE-05 was isolated in moderate yield (52% for 2 steps).

AGE-05:
$^1$H-RMN (500 MHz, $CDCl_3$): 3.62-3.78 (m, 20H); 4.04-4-10 (ddd, J=2.6, 5.6, 9.1, 1H), 4.41-4.47 (ddd, J=2.6, 7.2, 9.7, 1H), T31-7.40 (m, 3H), 7.46-7.52 (m, 2H); MS m/z calcd. for $[M+H]^+$: 293, found 293, 316(+Na) and 331 (+K).

Synthetic strategy for the preparation of the last key compound AGE-03 involved a six-steps procedure described in scheme 5.

In the first step, pentaethylene glycol was converted to its mono-protected derivative 2. Subsequent coupling with with t-butylbromoacetate afforded compound 14 with 76% yield. Saponification of this t-butyl ester derivative, followed by coupling of the obtained acid 15 with trichloroethanol, and removal of the alcohol protecting group gave key linear intermediate 16. Subsequent silyl ether deprotectection by TBAF treatment, was then immediately followed by cyclization reaction in high dilution conditions. Indeed, the deprotection reaction mixture was directly diluted, and $K_2CO_3$ was added. Finally, oxo-crown AGE-03 was obtained by this one-pot sequence with 61% yield from 16 after purification. NMR and MS data were in accord with the target structure.

EXAMPLE 3

Synthesis and Characterization of PLGA like Cyclic Polyesters

Scheme 6: overview or cyclic polyesters

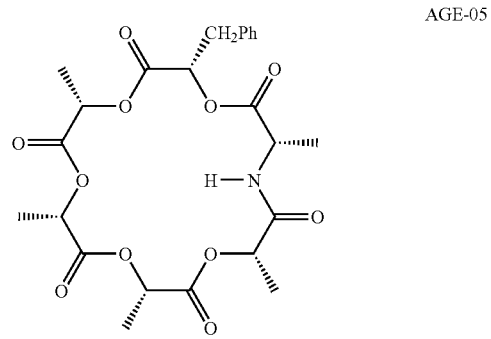

AGE-05

Scheme 5: synthesis of AGE-03

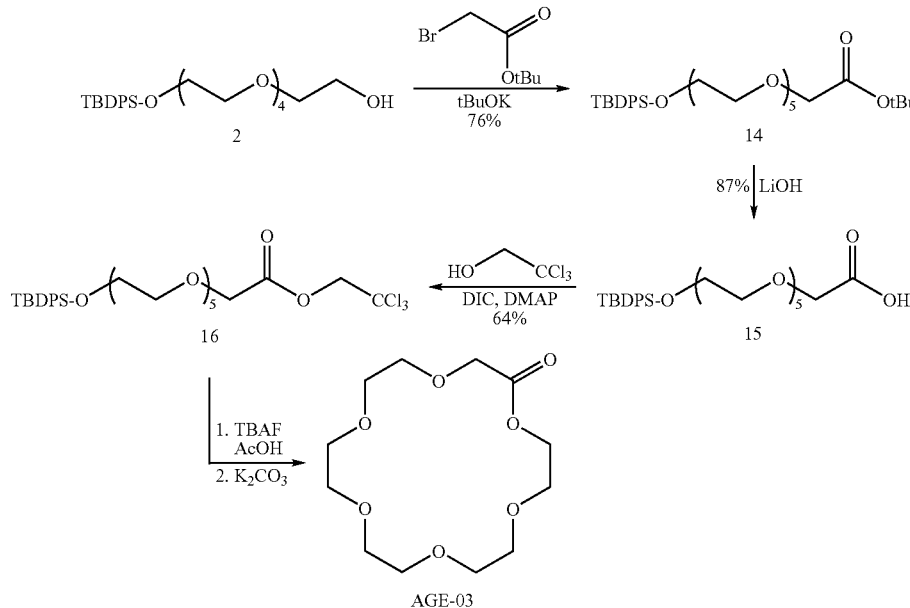

AGE-03

-continued

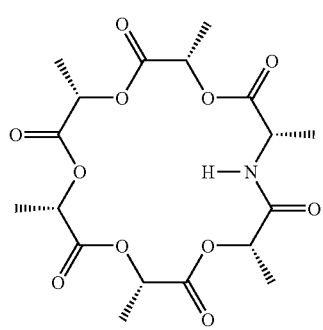
AGE-06

In order to set up and then optimize the preparation of cyclic oligoesters AGE-05 and AGE-06, it was decided to apply a solution-phase strategy, taking into account:

- the limited stability of the lactic acid derived building blocks as well as the obtained intermediates and formed ester bonds
- the risk of racemization if basic conditions were to be used, possibly leading to complex mixtures of diastereomers
- the compatibility of the hydroxy and acid protecting groups of the building blocks.

For these reasons, the THP group was choosen for hydroxy protection, whereas benzyl ester was used for acid function (benzyl lactate is commercially available). Synthetic converging 3+3 strategy is described in scheme 7. Target cyclic compounds include in their structure phenyllactic (AGE-05), lactic acid units as well as one Alanine residue (AGE-05 and AGE-06), thus comprising five ester and one amide bond. As shown in scheme 7, this latter was formed in the final key macrolactamization step.

Scheme 7: synthesis of AGE-04

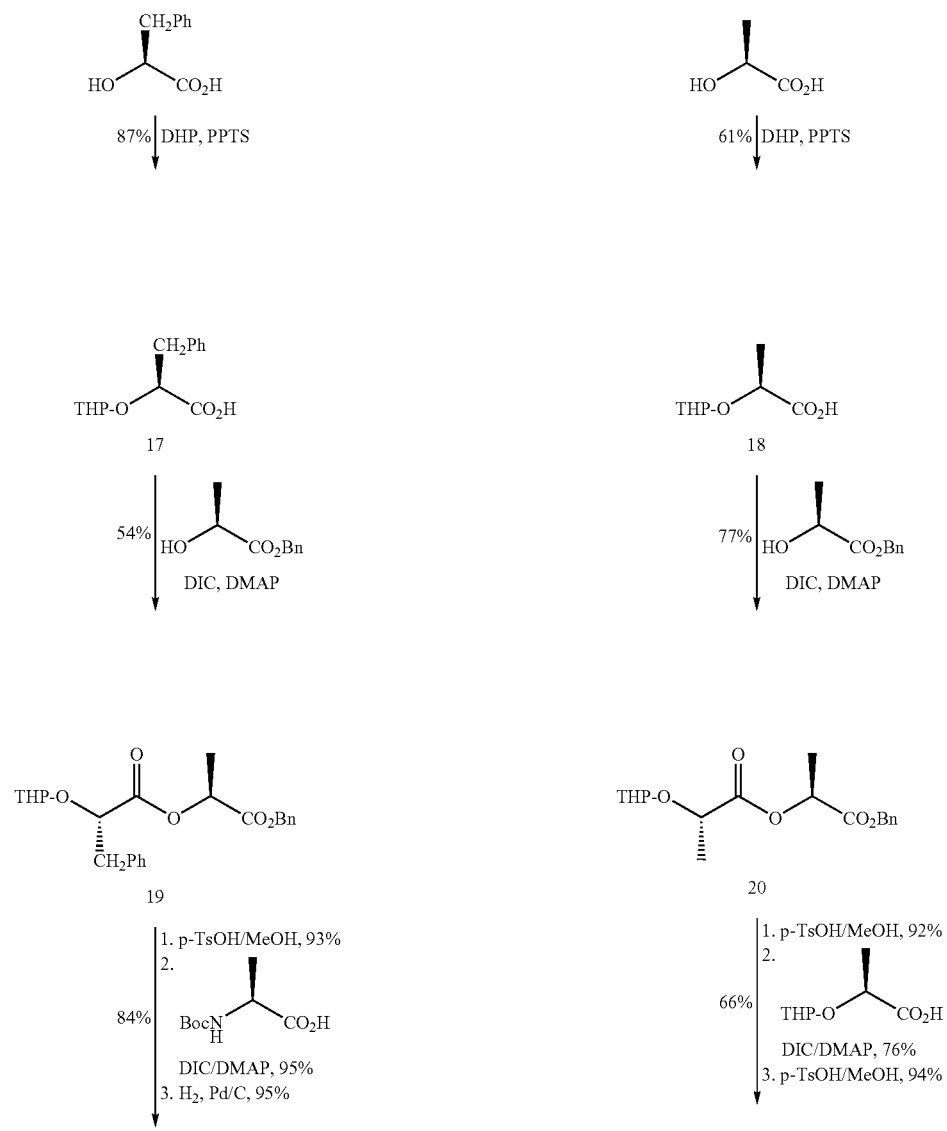

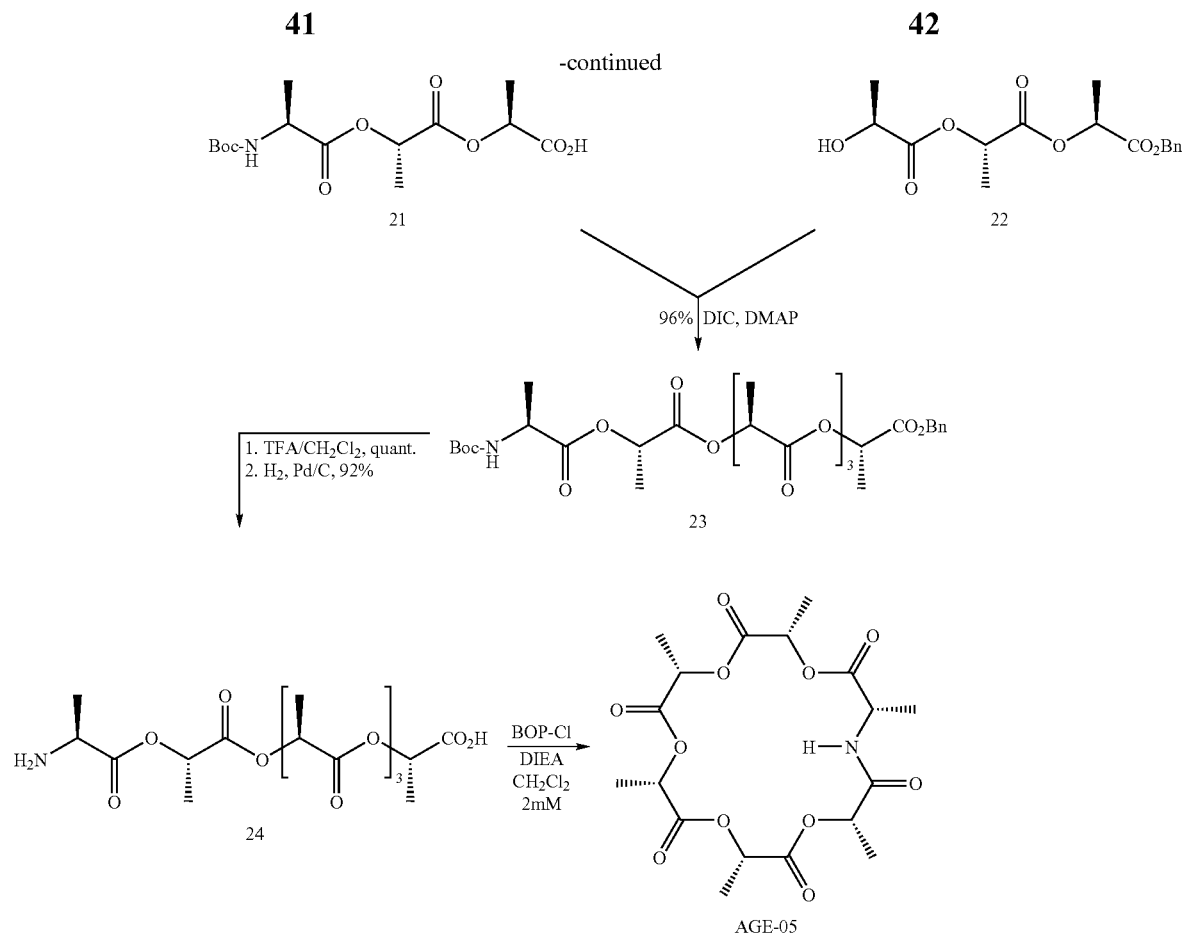

This synthetic pathway involved DIC/DMAP coupling conditions and mild protecting groups removals (p-TsOH/MeOH for THP group and Pd catalyzed hydrogenation for the benzyl one). Starting respectively from THP-protected phenyllactic and lactic acids 17 and 18, trimers 21 and 22 were prepared by a 4-steps procedure: coupling with benzyl lactate was followed by THP deprotection in acidic conditions, leading to compounds 19 and 20 which were reacted with either Boc-Ala-OH or O-THP protected lactic acid 18. Subsequent Boc or benzyl protecting groups deprotection by TFA treatment or hydrogenation in the presence of Pd/C gave respectively acid 21 or alcohol 22. Final coupling afforded fully protected hexamer 23, with 96% yield. Linear 23 was obtained with 12% overall yield for 11 steps. Boc deprotection by TFA treatment (10% in dichloromethane), followed by final debenzylation by hydrogenation afforded amino acid 24 which was used without any purification for macrolactamization reaction. This latter was performed using BOP-Cl reagent in high dilution conditions. Cyclic AGE-04 was then obtained with 35% overall yield from fully protected linear precursor (3 steps).

Using the same synthetic pathway, cyclic AGE-05 was prepared using lactic acid and Boc-Ala-OH as building blocks (scheme 8), 17% overall yield for the last three steps.

Scheme 8: synthesis of AGE-06

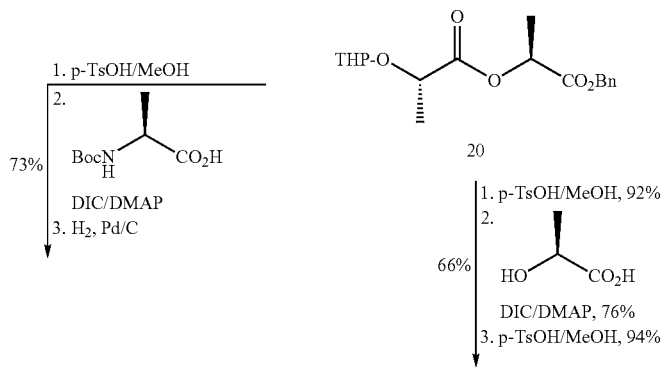

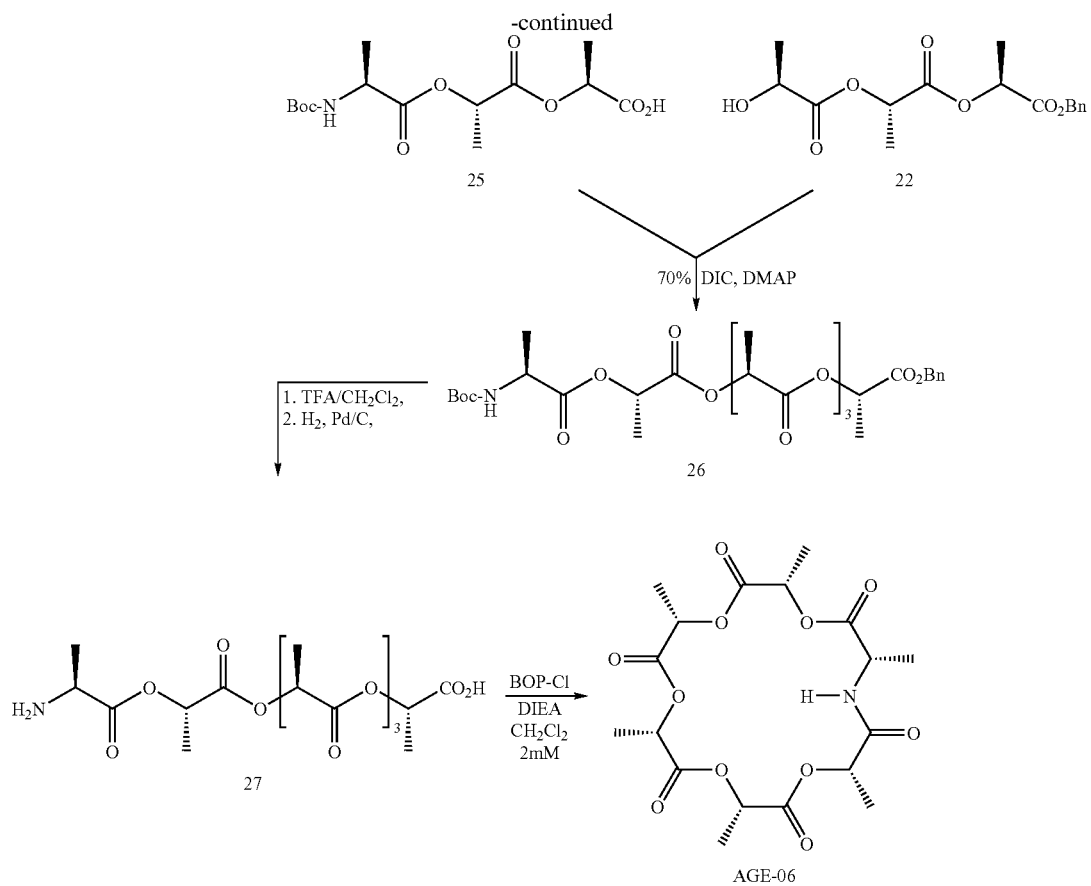

EXAMPLE 4

Use of Nonactine to Complex and Dissolve in Organic Medium the Protein Rantes

Two samples of 0.2 mg each of the folded protein Rantes were taken. One sample was used as standard and dissolved in a fixed volume (300 ul) of water/acetonitrile 50% v/v and 30 ul where injected onto HPLC (FIG. 6, HPLC section A).

The second sample was suspended in a mixture of DCM/MeOH 70%30% VN, (300 ul). The suspension with solid particles was centrifuged and the surnatant injected onto HPLC volume (30 ul). The HPLC trace showed no presence of the protein in the chromatogram (FIG. 6, HPLC section B).

Then, 2.0 mg of Nonactine were added and the mixture was vortexed. The suspension become a clear solution. Then, the mixture was centrifuged and 30 ul of the supernatant were injected onto HPLC. This time, the HPLC trace showed the presence of the peptide in similar proportion as per the area of the standard, thus proving the dissolution of the protein in the organic mixture (FIG. 6, HPLC section C). In the HPLC section C the protein has a different retention time (early elution) from the standard in section A. This phenomenon could be explained by the high percentage of organic solvents (like $CH_2Cl_2$ depicted in the figure) that carried through the protein complex with nonactine causing early elution.

EXAMPLE 5

Improvement of Delivery of Vasopressin and Glucagon

Vasopressin (9 amino acid peptide) and Glucagon (29 amino acid peptide) are (both) well known and studied molecules with a small molecular weight. The main interest in exploiting Vasopressin and Glucagon is the small size, making them a good model.

```
        Sequence of Vasopressin
  Cys Tyr Phe Gln Asn Cys Pro Arg Gly

Sequence of Glucagon
NH₂-H S Q G T F T S D Y A K Y L D S R R A Q D F V Q W L M N T-COOH
```

Underlined are residues with primary amine suitable for forming a complex with a polyester according to the invention. Bold and Italic are the residues with a carboxylate function (Aspartic acid and the Cα termini). The pI of the molecule is 6/5. Glucagon is a good model molecule since we can test the native molecule (above) as well as the pro-drug form for non-invasive delivery with the complexation strategy of the invention. Indeed, by mutating (via esterification) native carboxylic moieties (Aspartic residues, Cα) into pseudo-lysine (see below; thereby obtaining a pro-drug form) we significantly increase the number of sites available for complexation.

HSQGTFTS-$_{psd}$K-YAKYL-$_{pds}$KSRRAQ-$_{psd}$KFVQWLMNT-COO—CH$_2$—CO—Lys-NH$_2$ Thus, the combination of the complexation strategy with the ester pro-drug strategy generates a molecule that exhibits 7 side chains available for complexation. The prodrug peptide (with Asp residues and Cα transformed into a pseudo-lysines) complex with crown structures is significantly more soluble in the hydrophobic formulation medium. Thus, the higher concentration of the pro-drug peptide as well as its increased hydrophobicity leads to superior delivery across cell membranes. Standard tests to determine delivery across cell membrane include the CaCo-2 cell monolayer test (in vitro test; see J. E. Lopez, and N. A. Peppas, (2004), J. Biomater. Sci. Polymer Edn., 15, 385-396; J. F. Liang, V. C. Yang, (2005) Biochemical and Biophysical Research Communication, 335, 734-738). Alternatively or in addition, the colorimetric method of Z. Orynbayeva et. al. (2005) (Angew. Chem. Int. Ed., 44, 1092-1096) may be used.

EXAMPLE 6

Caco-2 Delivery Tests with Insulin Complex 18-Crown-6

In this Example, improved delivery of insulin to Caco-2 cells by using the crown ether(CE) 18-crown-6 is demonstrated.

In FIG. 7 HPLC chromatograms of the receiving chambers are shown. The receiving chamber collects the solution coming through Caco-2 cells. Should insulin pass through the Caco-2 cell lines, it is found in the receiving chamber.

Caco-2 Cells Insulin Delivery Protocol

Insulin Concentration: 3 mg in 125 µl of olive oil/Peg, 92%/8%, v/v

Vehicle: olive oil/Peg (esaethylenglycol)

Formulation agent: 18-crown-6

Positive control: Ibuprofen: 1 mg in 125 µl physiological buffer.

After vortex, 50 µl of the final mixture are added to the caco-2 cell well in double.

Active Sample Preparation (Insulin with Vehicle & Formulation Agent)

3 mg of Insulin previously desalted and 7.5 mg of 18-crown-6 are mixed in 200 µl of MeOH. After MeOH evaporation, 115 µl of olive oil and 10 µl Peg are added. Vortex for 2-3 minutes. After vortex, 50 µl of the final mixture are added to the Caco-2 cell well in double.

Control (Insulin with Formulation Agent in Physiological Buffer; No Organic or Non-Aqueous Vehicle Present)

7.5 mg of 18-crown-6 are dissolved in 0.2 ml of methanol and subsequently added to 3 mg of Insulin. Vortex the mixture for 2-3 minutes. The solution must be limpid. Then methanol is evaporated and 125 µl of physiological buffer are added; 50 µl of the above solution are added to the Caco-2 cell well in double.

Insulin at the same concentration in physiological buffer (without formulation agent and organic vehicle) does not cross caco-2 cells.

|  | PEG 25 ul | PEG 50 ul | Olive Oil + 5% PEG | Olive Oil + 10% PEG | Olive Oil + 20% PEG | Control |
|---|---|---|---|---|---|---|
| Series #1 | | | | | | |
| O.D. 570 nm | 0.694 | 0.598 | 1.142 | 0.913 | 0.819 | 1.787 |
| O.D. 630 nm | 0.211 | 0.195 | 0.351 | 0.298 | 0.27 | 0.635 |
| TEER t = 0 | 860 | 1250 | 1420 | 1260 | 1050 | 890 |
| Series #2 | | | | | | |
| O.D. 570 nm | 0.71 | 0.465 | 0.938 | 0.833 | 0.727 | 1.986 |
| O.D. 630 nm | 0.273 | 0.163 | 0.303 | 0.298 | 0.246 | 0.621 |
| TEER t = 0 | 1700 | 1200 | 1250 | 1280 | 1300 | 1430 |

The above table shows Caco-2 parameters when treated with different mixtures in presence of 18-Crown-6. TEER, which measures caco-2 cells tide junctions, proves Caco-2 tide junctions. O.D. measurements, after MTT treatment, indicates cell functionality.

EXAMPLE 7

Stability Tests of Oxo-Crown Ester in Human Plasma

The stability test of each oxo crown ether was performed using a concentration of 400 ng of oxocrown/ml of plasma. The plasma used for the test was a plasma pool. Samples were placed at 37° C. in an incubator with agitation. Then each time 20 µl of the plasma was treated with 80 µl of ACN centrifuge. 30 µl were injected to HPLC for analysis.

FIG. 8 shows the relative amount (in %) of oxo crown ether as a function of time.

Scheme 9: Ring opening products

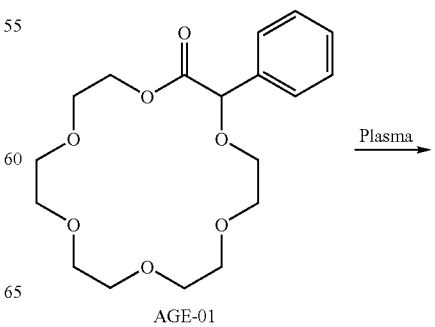

AGE-01

-continued

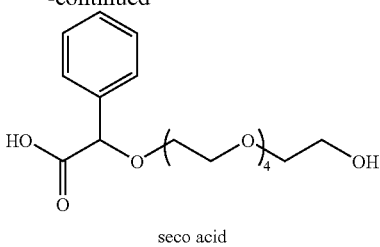

seco acid

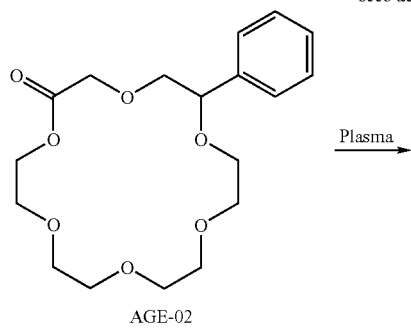

AGE-02

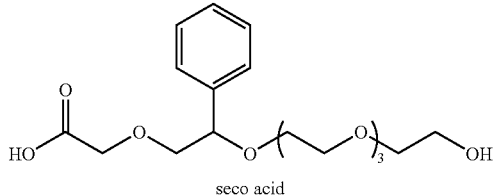

seco acid

EXAMPLE 8

In Vivo Delivery Tests on Mice by Sub-Lingual Administration

Dose 1: 0.5 mg of desalted human insulin with TFA counter-ions (corresponds to 0.4 mg of non treated standard insulin) are mixed with 60 mg of 18-crown-6. To these solids, 250 μl of a mixture is added, the mixture being composed of 200 μl of a 50% mixture of Propylen glycole and 50% glycerol, 200 mg of mono-decanoyl-glycerol and 100 μl of Cremofor EL. The final volume is approximately 310 μl.

Dose 2: 2.6 mg of desalted human insulin with TFA counter-ions are mixed with 60 mg of 18-crown-6. To these solids, 250 μl of a mixture is added, the mixture being composed of 200 μl of a 50% mixture of Propylen glycole and 50% glycerol, 200 mg of mono-decanoyl-glycerol and 100 μl of Cremofor EL. The final volume is approximately 310 μl.

Mice were treated with 6.5 μl of mixture 1 and 2, respectively. In dose 1, each mouse was treated with approximately 10 μg of desalted human insulin with TFA counter-ions (corresponds to 8 μg of non treated standard insulin). In dose 2, each mouse was treated with approximately 52 μg of desalted human insulin with TFA counter-ions (corresponds to 41.6 μg of non treated standard insulin). Data are shown in FIG. 9.

Results: Insulin Delivery is Measured by Blood Glucose Decrease.

The effect of dose 1 is close to the effects of IP injection. Since the dose 1 is approximately 7 times the dose injected as control, it is concluded that the actual delivery is around 10%. In case of dose 2, precipitation of insulin occurred, and samples had to be heated to regain solubility.

EXAMPLE 9

Insulin Delivery in Liposome on Caco-2 Cells

Liposomes were purchased from Sigma-Aldrich (pre-liposome formulation 8; product No. L3531) and used according to the following procedure. Alternatively, same ingredients were purchased by other suppliers (Avanti), and liposomes were prepared according the procedure indicated by Sigma. Insulin passage was measured by HPLC injection of samples in the receiving chamber.

Results: Human Insulin (h-insulin) incorporation into liposome according to Sigma preparation did not result measurable insulin passage through Caco-2 cells. The same amount of Insulin was complexed with 18-crown-6 and solubilized in organic solvent such as tert-butanol. The organic mixture containing insulin was mixed with the lipid mixture of Sigma, then solvent was evaporated or lyophilized. Water addition generated liposomes that were tested for delivery in Caco-2 cells. Complexation with 18-crown-6 showed an insulin peak in HPLC of the solution in the receiving chamber. Data are shown in FIG. 10.

FURTHER REFERENCES

Irie and Uekama (1999), Advanced Drug Delivery Reviews 36: 101-123.

Lifson, S., Felder, C. E. and Shanzer, A. (1983), J. Am. Chem. Soc, 105, 3866-3875.

Lifson, S., Felder, C. E. and Shanzer, A. (1984), J. Am. Chem. Soc, 23, 2577-2590.

McGeary and Bruget (2000). Tetrahedron 56: 8703-8713.

Challa et al. (2005). AAPS PharmSciTech 6: E329-E357.

The invention claimed is:

1. A method of manufacturing a pharmaceutical or diagnostic composition, said method comprising:

formulating in a non-aqueous hydrophobic delivery vehicle a complex comprising (i) an agent selected from calcitonin, glucagon, or vasopressin, or calcitonin, glucagon, or vasopressin having an esterified aspartic acid or glutamic acid residue, and (ii) a cyclic compound selected from:

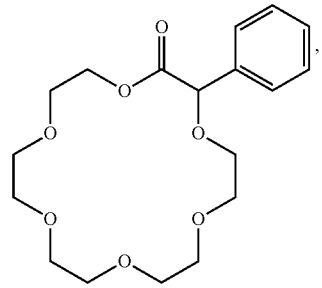
(AGE-01)

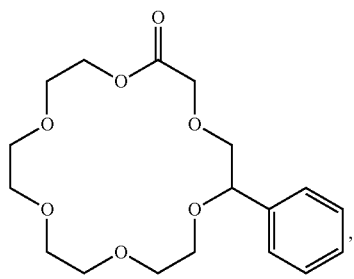
(AGE-02)

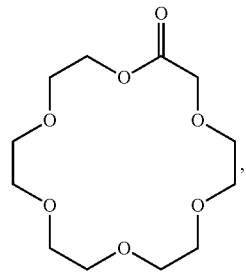
(AGE-03)

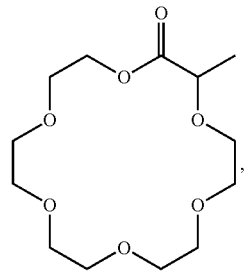
(AGE-04)

-continued (AGE-05)

(AGE-06)

wherein said cyclic compound is capable of forming a complex with a protonated primary and/or protonated secondary amino group and/or a protonated guanidinium group of said agent.

2. The method of claim 1, wherein said cyclic compound is biodegradable.

3. The method of claim 1, wherein formation of said complex is selective.

4. The method of claim 1, wherein said cyclic compound is (AGE-01)

5. The method of claim 1, wherein said cyclic compound is (AGE-02)

6. The method of claim 1, wherein said cyclic compound is (AGE-03)

7. The method of claim 1, wherein said active agent is calcitonin or calcitonin having an esterified aspartic acid or glutamic acid residue.

8. The method of claim 1, wherein said active agent is vasopressin or glucagon, or vasopressin or glucagon having an esterified aspartic acid or glutamic acid residue.

9. The method of claim 1, wherein said pharmaceutical or diagnostic composition is acidic.

10. The method of claim 9, wherein said pharmaceutical or diagnostic composition has a pH-value between 2 and 6.

11. The method of claim 1, wherein (i) an excess of said cyclic compound is used in forming said complex; and/or (ii) a second compound is further used in forming said complex.

12. A method of manufacturing a pharmaceutical or diagnostic composition, said method comprising:

formulating in a non-aqueous hydrophobic delivery vehicle a complex comprising (i) a metal ion, (ii) an agent selected from calcitonin, glucagon, or vasopressin, or calcitonin, glucagon, or vasopressin having an esterified aspartic acid or glutamic acid residue, and (iii) a cyclic compound selected from:

(AGE-01)

(AGE-02)

-continued

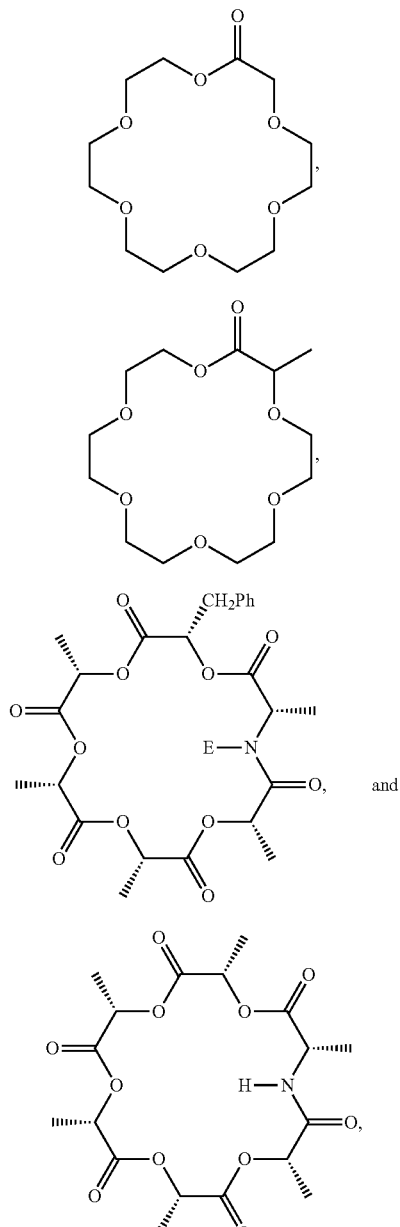

wherein said cyclic compound is capable of forming a complex with said metal ion, and said agent forming a salt with said metal ion.

13. The method of claim 12, wherein said cyclic compound is biodegradable.

14. The method of claim 12, wherein said cyclic compound is capable of selectively forming a complex with said metal ion.

15. The method of claim 1, wherein said pharmaceutical or diagnostic composition is a non-invasive delivery formulation.

16. A method of preparing a pharmaceutical or diagnostic composition with improved transmembrane and/or transmucosal delivery and/or improved stability, comprising the step of (a) bringing into contact a pharmaceutically or diagnostically active agent selected from calcitonin, glucagon, or vasopressin, or calcitonin, glucagon, or vasopressin having an esterified aspartic acid or glutamic acid residue with a cyclic compound, said cyclic compound selected from:

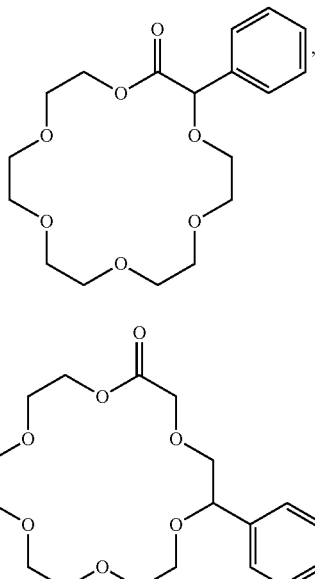

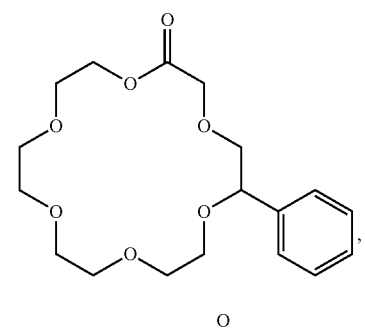

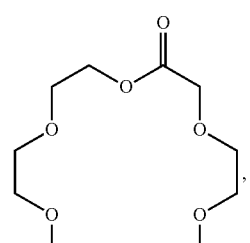

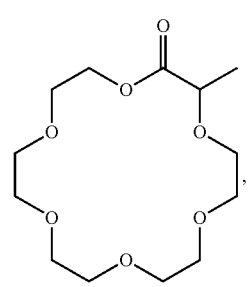

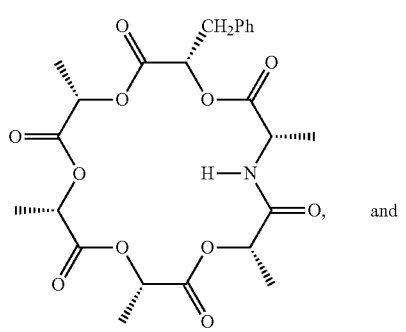

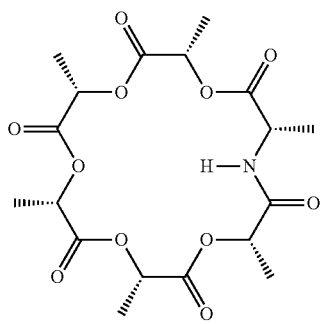
(AGE-06)

17. The method of claim 16, wherein an excess of said cyclic compound is used.

18. A pharmaceutical or diagnostic composition for improved transmembrane or transmucosal delivery of an agent, comprising a soluble complex of said agent and a cyclic compound in a hydrophobic vehicle, wherein (a) said agent is selected from calcitonin, glucagon, or vasopressin or calcitonin, glucagon, or vasopressin having an esterified aspartic acid or glutamic acid residue, (b) said cyclic compound is selected from:

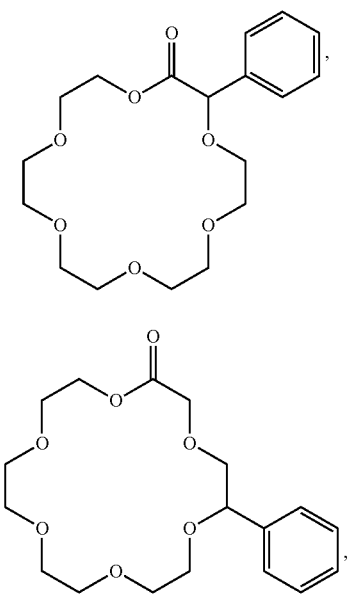
(AGE-01)

(AGE-02)

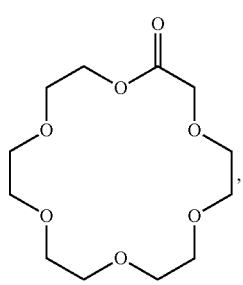
(AGE-03)

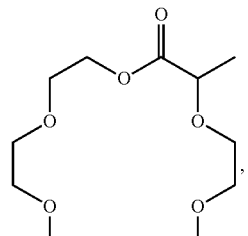
(AGE-04)

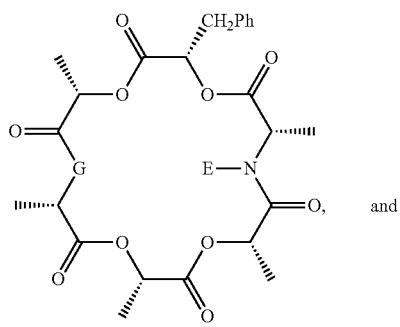
(AGE-05) and

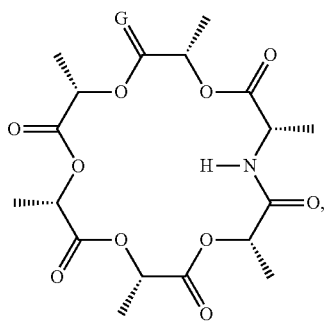
(AGE-06)

and capable of forming a stable complex with a metal cation and one or more of said primary and/or secondary protonated amino groups and/or protonated guanidinium groups, and (c) said hydrophobic vehicle is a non-aqueous composition comprising an organic solvent.

19. The pharmaceutical or diagnostic composition of claim 18, wherein said metal cation is a counter ion, and said composition comprises a soluble salt complex of said cyclic compound, said active agent, and said counter ion.

20. A method for transmembrane or transmucosal delivery of an active agent, comprising contacting a cell membrane or tissue mucosa with a pharmaceutical or diagnostic composition according to claim 18.

21. A method of producing a pharmaceutical or diagnostic composition for transmembrane or transmucosal delivery of an agent selected from calcitonin, glucagon, or vasopressin, or calcitonin, glucagon, or vasopressin having an esterified aspartic acid or glutamic acid residue, the method comprising:

(a) contacting said agent with a cyclic compound selected from:

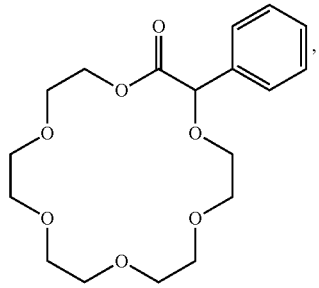 (AGE-01)

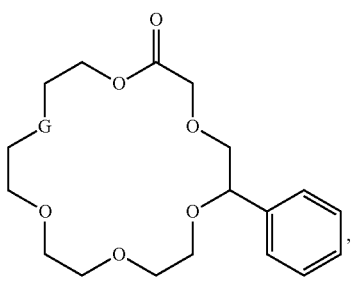 (AGE-02)

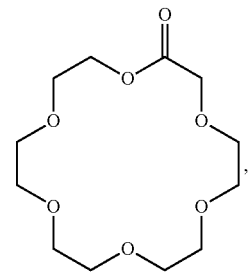 (AGE-03)

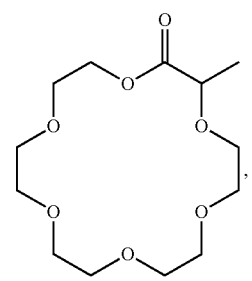 (AGE-04)

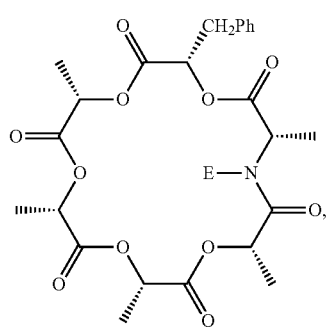 (AGE-05) and

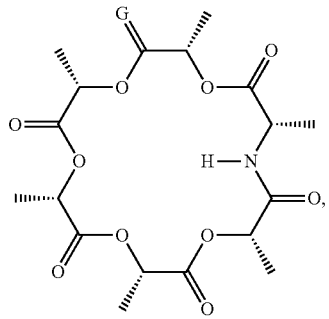 (AGE-06)

in an organic solvent to form a soluble complex of said cyclic compound and said agent, said cyclic compound, and capable of forming a complex with said agent;

(b) removing said organic solvent to form a solid comprising said agent in complex with said cyclic compound; and (c) solubilizing said solid in a hydrophobic vehicle comprising a non-aqueous solvent capable of solubilizing said solid and transmembrane or transmucosal delivery of said active agent.

22. The pharmaceutical or diagnostic composition of claim 18, wherein said cyclic compound is

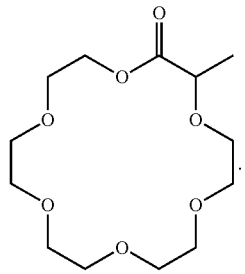 (AGE-04)

23. The pharmaceutical or diagnostic composition of claim 18, wherein said cyclic compound is

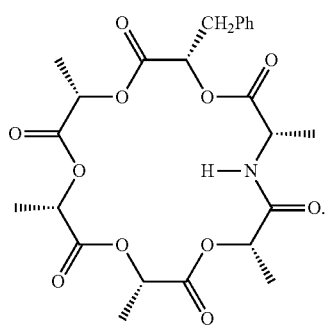 (AGE-05)

24. The pharmaceutical or diagnostic composition of claim 18, wherein said cyclic compound is

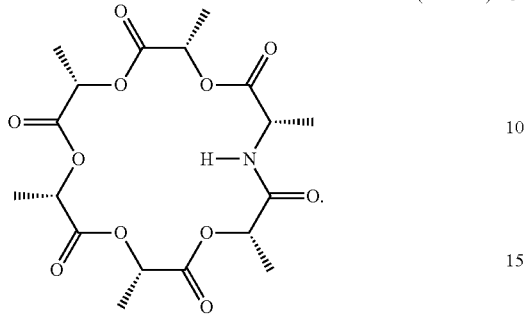

(AGE-06)

25. The pharmaceutical or diagnostic composition of claim 18, wherein the agent is calcitonin, or calcitonin having an esterified aspartic acid or glutamic acid residue.

26. The pharmaceutical or diagnostic composition of claim 18, wherein the agent is glucagon, or glucagon having an esterified aspartic acid or glutamic acid residue.

27. The pharmaceutical or diagnostic composition of claim 18, wherein the agent is vasopressin, or vasopressin having an esterified aspartic acid or glutamic acid residue.

* * * * *

SEQUENCE LISTING

```
<160> NUMBER OF SEQ ID NOS: 3

<210> SEQ ID NO 1
<211> LENGTH: 69
<212> TYPE: PRT
<213> ORGANISM: Artificial Sequence
<220> FEATURE:
<223> OTHER INFORMATION: Description of Artificial Sequence: Model
      chemokine called M8

<400> SEQUENCE: 1

Met Ser Pro Pro Leu Met Gln Thr Thr Pro Cys Cys Phe Ala Tyr Ile
1               5                   10                  15

Ala Arg Pro Leu Pro Arg Ala His Ile Lys Glu Tyr Phe Tyr Thr Ser
```

```
            20                  25                  30
Gly Lys Cys Ser Asn Pro Ala Val Val Phe Val Thr Arg Lys Asn Arg
        35                  40                  45

Gln Val Cys Ala Asn Pro Glu Lys Lys Trp Val Arg Glu Tyr Ile Asn
    50                  55                  60

Ser Leu Glu Met Ser
65

<210> SEQ ID NO 2
<211> LENGTH: 9
<212> TYPE: PRT
<213> ORGANISM: Homo sapiens

<400> SEQUENCE: 2

Cys Tyr Phe Gln Asn Cys Pro Arg Gly
1               5

<210> SEQ ID NO 3
<211> LENGTH: 29
<212> TYPE: PRT
<213> ORGANISM: Homo sapiens

<400> SEQUENCE: 3

His Ser Gln Gly Thr Phe Thr Ser Asp Tyr Ala Lys Tyr Leu Asp Ser
1               5                   10                  15

Arg Arg Ala Gln Asp Phe Val Gln Trp Leu Met Asn Thr
            20                  25
```